US009198927B2

(12) United States Patent
McCallus et al.

(10) Patent No.: US 9,198,927 B2
(45) Date of Patent: Dec. 1, 2015

(54) TARGETING OPPOSITE STRAND REPLICATION INTERMEDIATES OF SINGLE-STRANDED VIRUSES BY RNAI

(75) Inventors: Daniel E. McCallus, Cambridge, MA (US); Catherine Pachuk, Northborough, MA (US); Baohua Gu, Malvern, PA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 12/714,949

(22) Filed: Mar. 1, 2010

(65) Prior Publication Data

US 2010/0267805 A1 Oct. 21, 2010

Related U.S. Application Data

(63) Continuation of application No. 12/201,499, filed on Aug. 29, 2008, now abandoned, which is a continuation of application No. 11/663,593, filed as application No. PCT/US2005/034371 on Sep. 26, 2005, now abandoned.

(60) Provisional application No. 60/613,065, filed on Sep. 24, 2004.

(51) Int. Cl.
| *C12N 15/11* | (2006.01) |
| *A61K 31/713* | (2006.01) |
| *C12N 15/113* | (2010.01) |
| *C07H 21/04* | (2006.01) |

(52) U.S. Cl.
CPC .......... *A61K 31/713* (2013.01); *C12N 15/1131* (2013.01); *C12N 2310/111* (2013.01); *C12N 2310/14* (2013.01); *C12N 2310/53* (2013.01)

(58) Field of Classification Search
None
See application file for complete search history.

(56) References Cited

U.S. PATENT DOCUMENTS

| 5,837,463 | A | | 11/1998 | Tanaka et al. |
| 5,874,565 | A | * | 2/1999 | Rice et al. ................... 536/24.1 |
| 6,107,028 | A | | 8/2000 | Kay et al. |
| 7,727,970 | B2 | * | 6/2010 | Roelvink et al. ............ 514/44 R |
| 2004/0091457 | A1 | | 5/2004 | John et al. |
| 2004/0127446 | A1 | * | 7/2004 | Blatt et al. ....................... 514/44 |
| 2004/0209831 | A1 | | 10/2004 | McSwiggen et al. |
| 2004/0242518 | A1 | | 12/2004 | Chen et al. |
| 2005/0008617 | A1 | * | 1/2005 | Chen et al. ................... 424/93.2 |
| 2008/0070854 | A1 | * | 3/2008 | Pachuk et al. ................... 514/44 |

FOREIGN PATENT DOCUMENTS

| WO | 94/05813 A | 3/1994 |
| WO | WO 9904008 A2 * | 1/1999 |
| WO | 03/033700 | 4/2003 |
| WO | 2004/011647 A | 2/2004 |
| WO | 2004/028471 A | 4/2004 |
| WO | 2004/029213 | 4/2004 |
| WO | 2004/078974 A | 9/2004 |
| WO | 2005/014806 A | 2/2005 |
| WO | 2005/087926 | 9/2005 |
| WO | 2006/069064 | 6/2006 |

OTHER PUBLICATIONS

Randall, G. et al., Virus Research, 102(1):19-25 (2004). "Interfering with hepatitis C virus RNA replication.".
Schwarz, D.S. et al., Cell, 115:199-208 (2003). "Asymmetry in the assembly of the RNAi enzyme complex."
Ge, Q. et al., PNAS, 100(5):2718-2723 (2003). "RNA interference of influenza virus production by directly targeting mRNA for degradation and indirectly inhibiting all viral RNA transcription."
Friebe, P. et al., Journal of Virology, 76(11):5326-5338 (2002). "Genetic analysis of sequences in the 3' nontranslated region of hepatitis C virus that are important for RNA replication."
Kronke, J. et al., Journal of Virology, 78(7):3436-3446 (2004). "Alternative approaches for efficient inhibition of hepatitis C virus RNA replication by small interfering RNAs."
Yokota, T. et al., EMBO Reports, 4(6):602-608 (2003). "Inhibition of intracellular hepatitis C virus replication by synthetic and vector-derived small interfering RNAs."

* cited by examiner

*Primary Examiner* — Dana Shin
(74) *Attorney, Agent, or Firm* — Nixon Peabody LLP; Mark J. FitzGerald

(57) ABSTRACT

The invention relates to methods and compositions for modulating viral replication through double-stranded RNA-mediated gene silencing (RNAi), wherein the antiviral methods and compositions preferentially target opposite strand replication intermediates of single-stranded RNA viruses.

21 Claims, 3 Drawing Sheets

TARGETING OPPOSITE STRAND REPLICATION INTERMEDIATES OF SINGLE-STRANDED VIRUSES BY RNAI

CROSS-REFERENCE TO RELATED APPLICATIONS

This application is a Continuation of U.S. patent application Ser. No. 12/201,499 filed on Aug. 29, 20084, which is a Continuation of U.S. patent application Ser. No. 11/663,593 filed on Mar. 23, 2007, now abandoned, which is a 35 U.S.C. 371 National Entry of International Application No. PCT/US2005/034371 filed on Sep. 26, 2005, which designated the United States and which claims the benefit of priority under 35 U.S.C. §119(e) of U.S. Provisional Application No. 60/613,065 filed on Sep. 24, 2004, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Apr. 12, 2011, is named 20110502_SequenceListing_TextFile_051058_037200_C.txt and is 15,796 bytes in size.

FIELD OF THE INVENTION

The invention relates to methods and compositions for inhibiting, suppressing, or down-regulating viral replication through double-stranded RNA-mediated gene silencing (RNAi), wherein the antiviral methods and compositions preferentially target opposite strand replication intermediates of single-stranded viruses.

BACKGROUND OF THE INVENTION

There has been considerable interest in developing nucleic acid based compositions for anti-viral applications, including antisense compositions, double-stranded RNA based compositions, triplex-forming oligonucleotides, ribozymes, etc. Their sequence-specific mode of action holds out the promise of therapeutics having a high level of safety and efficacy. Currently accepted methods of down-regulating viral RNAs of plus strand viruses largely involve directly targeting the plus strand RNAs. For example, antisense oligonucleotides are believed to work by hybridizing to an mRNA, thereby interfering with translation of the mRNA into protein. Antisense oligonucleotides are therefore usually designed to be complementary to a target mRNA. U.S. Pat. No. 6,001,990, for example, "Antisense inhibition of hepatitis C virus", describes oligonucleotides substantially complementary to sequences of the HCV genomic RNA, i.e., sequences which are complementary to and target the plus strand of the HCV genome. Similarly, it has been thought that RNAi is mechanistically connected to translation so that RNAs that are not translated are refractory to siRNA inhibition, while those that are actively translated are effective targets. See Wang and Carmichael, Microbial. Mol. Biol. Rev. 68: 432-452 (2004) See also, e.g., Yokota at al., EMBO Rep. 4:602-08 (2003), describing siRNA targeting of the 5' UTR of the HCV genomic RNA. Krönke at al., J. Virol. 78 (7): 3436-46 (2004), evaluated siRNAs directed against HCV genomic RNA including various regions of the coding sequence as well the 5' NTR, and reported that large sections of the NTRs are resistant to RNAi. They speculated, however, that one sequence directed to the 5' NTR may actually have targeted the 3' terminus of the negative strand, possibly contributing to its antiviral activity. Ribozymes appear to be an exception to plus-strand HCV targeting, with U.S. Pat. No. 6,107,028 describing ribozymes targeting the plus and/or negative strands of HCV.

A large number of viruses of clinical relevance produce RNA molecules during replication that are not messenger RNA molecules. For example, positive or plus-strand RNA viruses such as hepatitis C(HCV) generate a so-called negative or minus strand RNA which is complementary to and of opposite polarity (5' vs. 3' ends) than the various mRNAs made by the virus. The extreme sequence variability and high rate of mutation of RNA viruses such as HCV provide an impetus to target conserved regions of the viral genomic RNA. However, the complex secondary structure of conserved regions of HCV as well as the presence of cellular and viral proteins binding to these conserved regions in the intracellular environment creates uncertainty as to the applicability of nucleic acid based antiviral approaches to these otherwise preferred target regions. Smith et al. mapped conserved regions of both the plus and minus strands of HCV to determine secondary structure and hybridization accessibility to antisense constructs. See, J. Virol. 76 (19): 9563-74 (2002), "Secondary Structure and Hybridization Accessibility of Hepatitis C Virus 3'-Terminal Sequences", also Smith et al., J. Viral Hepat., 11 (2): 115-23 (2004).

Similarly, RNA interference (RNAi) has been used to target the selective destruction of mRNA molecules produced by viruses in strategies aimed at creating effective anti-viral agents. Like antisense, dsRNA-mediated RNAi relies on sequence-specific nucleic acid interactions, but the involvement of the multiprotein RNA-induced silencing complex (RISC) makes it unclear whether antisense accessibility alone correlates to target accessibility for RNAi degradation. Furthermore, since RNAi strategies employ double-stranded RNA molecules (dsRNA), which contain sequences both identical to and complementary to a viral target, a method of targeting e.g. minus-strand RNA in preference to its complementary viral mRNA has not been demonstrated. In turn, the potency of an anti-viral agent that works by selectively targeting e.g. the minus strand (of a plus-strand RNA virus) instead of its mRNA or protein products, has not previously been shown. The present invention provides a method for using RNAi to preferentially target the destruction of e.g. the minus strand of a plus-strand RNA virus, and also provides novel compositions based on this method for potent inhibition of the replication of RNA viruses such as HCV.

SUMMARY OF THE INVENTION

The currently accepted application of RNA interference (RNAi) mediated by double-stranded RNA (dsRNA) has been largely restricted to target molecules classified as messenger RNA (mRNA). It has been thought that RNAi is mechanistically connected to translation so that RNAs that are not translated are refractory to siRNA inhibition, while those that are actively translated are more effective targets. See Wang and Carmichael, Microbiol. Mol. Biol. Rev. 68: 432-452 (2004). Although a number of viruses (particularly RNA viruses known as plus-strand viruses) also produce RNA molecules that are not mRNA, strategies to inhibit viral functions using dsRNA have targeted the mRNA (or the analogous genomic RNA) produced by the virus, including coding sequences as well as untranslated regions. See, e.g., Yokota et al., EMBO Rep. 4:602-08 (2003); Kapadia et al., Proc. Natl. Acad. Sci. USA 100(4):2014-18 (2003); Wilson et al., J. Virol. 79 (11): 7050-58 (2005); Krönke et al., J. Virol. 78(7):3436-46 (2004).

In contrast, the anti-viral methods and compositions of the invention target the minus strand RNAs of plus strand viruses and the plus strand RNAs of minus strand viruses. With respect to minus strand viruses, it is advantageous to target plus strand non-mRNA sequences, which are usually much less abundant than the viral mRNAs. Applicants have discovered that, surprisingly, superior anti-viral activity can be achieved by targeting the "opposite" strand replication intermediate (anti-genomic RNA strand) of these viruses, i.e., targeting the minus strand of plus-strand viruses and the plus strand of minus-strand viruses. Not only are such dsRNA molecules designed to preferentially target the opposite strand highly active, but utilizing the opposite strand as the starting point for dsRNA design results in a greater proportion of active molecules. This approach has the distinct advantage of destroying or down-regulating a population of RNAs which is less abundant than the corresponding major strand message. This means that a lower amount of effector double-stranded RNA will be required to achieve the desired goal of eliminating the virus. Because these "opposite" strands are a necessary intermediate for viral replication, the destruction or down-regulation of these strands will lead to a decrease or elimination of viral replication. Utilization of the "opposite" strand as a target for RNAi attack also provides for an expanded range of potential antiviral targets and thus an expanded range of potential agents active against a particular virus. Considering the high mutation rate of RNA viruses such as HCV, effective anti-viral therapy necessitates utilization of a multi-drug regimen. In one aspect, therefore, one or more of such negative-strand targeting dsRNAs may be used, either alone, or in combination with one or more dsRNAs which preferentially target the plus strand, and/or with other antiviral agents.

Plus strand viruses such as but not limited to picornaviruses, calciviruses, astroviruses, togaviruses, flaviviruses, coronaviruses and arteriviruses are single-stranded RNA viruses whose RNA genome is in the sense polarity, meaning that their RNA genome is in the same polarity as messenger RNAs that encode their viral proteins. These "plus strand" viruses all replicate through a minus strand intermediate that is usually much less abundant compared to the levels of plus strands in infected cells. For example, in Hepatitis C (flavivirus) infected cells, the minus strand is present at about 1/30 the level of plus strand RNA molecules. The lower number of minus strands coupled with the fact that the minus strand is required for viral replication makes targeting the minus strand by RNAi ideal as a therapeutic strategy. In some applications, effective antiviral strategies will involve concurrent use of multiple RNAi agents, including one, two, three or more negative strand targeting dsRNA molecules, either alone, or in combination with other antiviral agents, including, e.g., one, two, three or more positive strand targeting dsRNA molecules.

In some applications of the invention, it is desirable instead to target segments of the plus strand of minus strand viruses. Minus strand viruses such as paramyxoviruses, rhabdoviruses, filoviruses, orthomyxoviruses, bunyaviruses and arenaviruses are single-stranded RNA viruses whose genome is of negative polarity. These viruses all replicate through a plus strand intermediate that is distinct from the mRNA products of the virus, and that is usually much less abundant compared to the levels of minus strand RNAs in cells. The relatively low number of plus strands coupled with the fact that the plus strand is required for viral replication makes targeting the plus strand of these viruses by RNAi promising as a novel therapeutic strategy.

One aspect of this invention is to provide a method of treating an infection of a vertebrate cell by a single-stranded RNA virus comprising administering to said vertebrate cell an RNA effector molecule comprising an Effector Sequence of at least 19 contiguous nucleotides from a reverse complement to an opposite strand replication intermediate of said single-stranded virus.

A further aspect of the invention is to provide a method of modulating replication of a single-stranded RNA virus in a target vertebrate cell comprising administering to the cell a double-stranded RNA effector molecule comprising:
 a) an at least 19 contiguous nucleotide Effector Sequence which is a reverse complement to an opposite strand replication intermediate of the single-stranded RNA virus,
 b) an Effector Complement which is the reverse complement of the Effector Sequence,
and wherein said Effector Sequence preferentially associates with the RISC relative to the Effector Complement.

In another aspect, multiple antiviral double-stranded RNA effector molecules will be provided concurrently to a vertebrate cell, including one, two, three or more of said double-stranded RNA effector molecules each comprising an at least 19 contiguous nucleotide Effector Sequence which is a reverse complement to an opposite strand replication intermediate of a single-stranded RNA virus and which preferentially associates with the RISC relative to its Effector Complement, either alone, or in combination with one or more other antiviral agents, including, e.g., one, two, three or more double-stranded RNA effector molecules each comprising an at least 19 contiguous nucleotide Effector Sequence which is an reverse complement of the genomic RNA strand of a single-stranded RNA virus and an Effector Complement which is the reverse complement of the Effector Sequence, and wherein the Effector Sequence preferentially associates with the RISC relative to the Effector Complement.

Another aspect of the invention is to provide to a vertebrate cell one or more of such double-stranded RNA effector molecules each comprising an at least 19 contiguous nucleotide Effector Sequence which is a reverse complement to an opposite strand replication intermediate of a single-stranded RNA virus. Preferably, the reverse complement has an A or U at position 1 of the 5' end of said reverse complement and the double-stranded RNA effector molecule has a lower thermal stability (Tm) at the terminus comprising the 5' end of the Effector Sequence compared to the terminus comprising the 3' end of the Effector Sequence.

Another aspect of the invention is to provide to a vertebrate cell one or more, preferably two, three or more, of such double-stranded RNA effector molecules each comprising an at least 19 contiguous nucleotide Effector Sequence which is a reverse complement to an opposite strand replication intermediate (anti-genomic RNA) of a single-stranded RNA virus, e.g., the anti-genomic minus strand of a plus strand RNA virus, or the anti-genomic plus strand or non-mRNA sequences of a minus strand virus, and wherein the double-stranded RNA effector molecule directly targets said anti-genomic minus strand or said anti-genomic plus strand, respectively. In a preferred aspect said double-stranded RNA effector molecules are provided by providing to the vertebrate cell an expression construct encoding the double-stranded RNA effector molecules. Other objects and advantages of the present invention will become apparent to those skilled in the art upon reference to the detailed description that hereinafter follows.

BRIEF DESCRIPTION OF THE SEQUENCES

SEQ ID NO:1 represents nucleotides 9382-9402 of the HCV 3' NTR.
SEQ ID NO:2 represents nucleotides 9502-9522 of the HCV 3' NTR.
SEQ ID NO:3 represents nucleotides 9512-9532 of the HCV 3' NTR.
SEQ ID NO:4 represents nucleotides 9518-9538 of the HCV 3' NTR.
SEQ ID NO:5 represents nucleotides 9525-9545 of the HCV 3' NTR.
SEQ ID NO:6 represents nucleotides 9526-9546 of the HCV 3' NTR.
SEQ ID NO:7 represents nucleotides 9552-9572 of the HCV 3' NTR.
SEQ ID NO:8 represents nucleotides 9577-9597 of the HCV 3' NTR.
SEQ ID NO:9 represents nucleotides 9579-9599 of the HCV 3' NTR.
SEQ ID NO:10 represents nucleotides 9583-9603 of the HCV 3' NTR.
SEQ ID NO:11 represents nucleotides 9509-9529 of the HCV 3' NTR.
SEQ ID NO:12 represents nucleotides 9520-9540 of the HCV 3' NTR.
SEQ ID NO:13 represents nucleotides 9534-9554 of the HCV 3' NTR.
SEQ ID NO:14 represents nucleotides 9560-9580 of the HCV 3' NTR.
SEQ ID NO:15 represents nucleotides 9581-9601 of the HCV 3' NTR.
SEQ ID NO:16 represents nucleotides 9506-9526 of the HCV 3' NTR.
SEQ ID NO:17 represents nucleotides 9514-9534 of the HCV 3' NTR.
SEQ ID NO:18 represents nucleotides 9520-9540 of the HCV 3' NTR.
SEQ ID NO:19 represents nucleotides 9537-9557 of the HCV 3' NTR.
SEQ ID NO:20 represents nucleotides 9544-9563 of the HCV 3' NTR.
SEQ ID NO:21 represents nucleotides 9554-9574 of the HCV 3' NTR.
SEQ ID NO:22 represents nucleotides 9567-9587 of the HCV 3' NTR.
SEQ ID NO:23 represents nucleotides 9584-9604 of the HCV 3' NTR.
SEQ ID NO:24 represents an HCV 5' UTR siRNA (region 1 plus strand).
SEQ ID NO:25 represents an HCV 5' UTR siRNA (region 1 minus strand).
SEQ ID NO:26 represents an HCV 5' UTR siRNA (region 1 plus strand).
SEQ ID NO:27 represents an HCV 5' UTR siRNA (region 1 minus strand).
SEQ ID NO:28 represents an HCV 5' UTR siRNA (region 1 plus strand).
SEQ ID NO:29 represents an HCV 5' UTR siRNA (region 1 minus strand).
SEQ ID NO:30 represents an HCV 5' UTR siRNA (region 1 plus strand).
SEQ ID NO:31 represents an HCV 5' UTR siRNA (region 1 minus strand).
SEQ ID NO:32 represents an HCV 5' UTR siRNA (region 1 plus strand).
SEQ ID NO:33 represents an HCV 5' UTR siRNA (region 1 minus strand).
SEQ ID NO:34 represents an HCV 5' UTR siRNA (region 1 plus strand).
SEQ ID NO:35 represents an HCV 5' UTR siRNA (region 1 minus strand).
SEQ ID NO:36 represents an HCV 5' UTR siRNA (region 1 plus strand).
SEQ ID NO:37 represents an HCV 5' UTR siRNA (region 1 minus strand).
SEQ ID NO:38 represents an HCV 5' UTR siRNA (region 2 plus strand).
SEQ ID NO:39 represents an HCV 5' UTR siRNA (region 2 minus strand).
SEQ ID NO:40 represents an HCV 5' UTR siRNA (region 2 plus strand).
SEQ ID NO:41 represents an HCV UTR siRNA (region 2 minus strand).
SEQ ID NO:42 represents an HCV 5' UTR siRNA (region 2 plus strand).
SEQ ID NO:43 represents an HCV 5' UTR siRNA (region 2 minus strand).
SEQ ID NO:44 represents an HCV 5' UTR siRNA (region 2 plus strand).
SEQ ID NO:45 represents an HCV 5' UTR siRNA (region 5 plus strand).
SEQ ID NO:46 represents an HCV 5' UTR siRNA (region 5 minus strand).
SEQ ID NO:47 represents an HCV 5' UTR siRNA (region 5 plus strand).
SEQ ID NO:48 represents an HCV 5' UTR siRNA (region 5 minus strand).
SEQ ID NO:49 represents an HCV 5' UTR siRNA (region 5 plus strand).
SEQ ID NO:50 represents an HCV 5' UTR siRNA (region 5 minus strand).
SEQ ID NO:51 represents an HCV 5' UTR siRNA (region 5 plus strand).
SEQ ID NO:52 represents an HCV 5' UTR siRNA (region 5 minus strand).
SEQ ID NO:53 represents an HCV 5' UTR siRNA (region 5 plus strand).
SEQ ID NO:54 represents an HCV 5' UTR siRNA (region 5 minus strand).
SEQ ID NO:55 represents an HCV 5' UTR siRNA (region 5 plus strand).
SEQ ID NO:56 represents an HCV 5' UTR siRNA (region 5 minus strand).
SEQ ID NO:57 represents an HCV 5' UTR siRNA (region 5 minus strand).
SEQ ID NO:58 represents an HCV 5' UTR siRNA (region 5 minus strand).
SEQ ID NO:59 represents an HCV 3' UTR conserved region sequence.

DETAILED DESCRIPTION OF THE INVENTION

Figure 1:
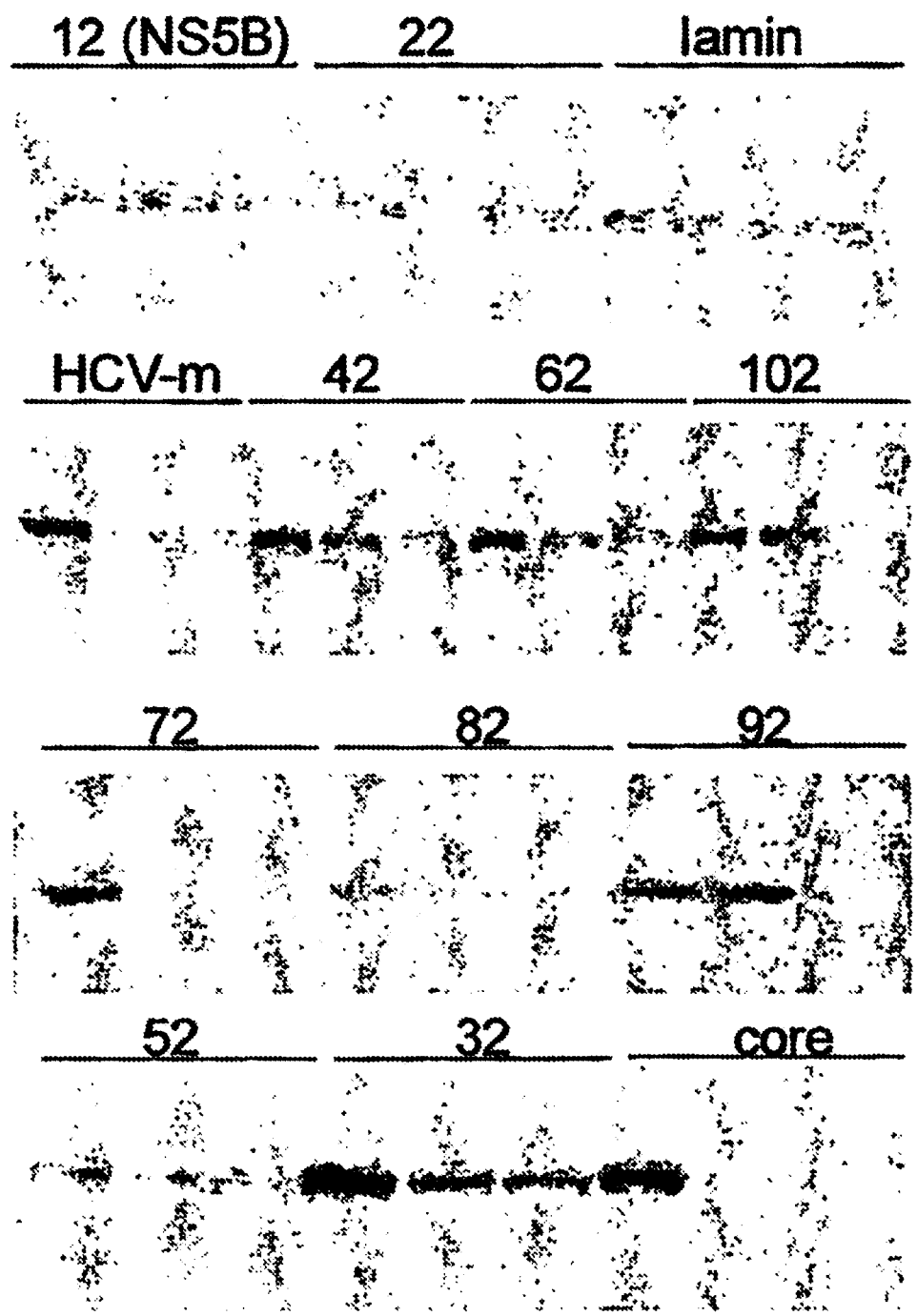
FIG. 1 is a Western Blot showing levels of HCV NS5A protein at (left to right) 0, 9, and 20 pmole of the identified siRNAs.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

RNA interference (RNAi) is the process of sequence-specific, post-transcriptional gene silencing or transcriptional gene silencing in animals and plants, initiated by double-stranded RNA (dsRNA) that is homologous in sequence to the silenced gene. Since RNA interference acts in a sequence specific manner, the RNAi molecule used as a drug must be specific to its target. It is known in the art that viral genomes, especially RNA viral genomes, are variable to accommodate resistance to changes in the environment. Thus, in order to knock down viral genome replication using RNAi, there is a need to identify conserved and unique regions in the viral genome. It is also important to ensure that conserved viral sequences targeted for silencing according to the invention be substantially non-homologous to any naturally occurring, normally functioning, host polynucleotide sequence, so that the dsRNA molecule does not adversely affect the function of any essential, naturally occurring, host polynucleotide sequences, when used in the methods of this invention. Such naturally occurring functional polynucleotide sequences include sequences that encode desired proteins, as well as sequences that are non-coding but essential regulatory sequences in a healthy host organism. Thus, the preferred RNA effector molecules useful in this invention must be sufficiently distinct in sequence from any host polynucleotide sequences for which function is intended to be undisturbed after any of the methods of this invention are performed. Computer algorithms may be used to define the essential lack of homology between the RNA molecule polynucleotide sequence and host, essential, normal sequences.

In the context of this disclosure, a number of terms shall be utilized. By "at least 19 contiguous nucleotides" is meant that a nucleotide sequence can start at any nucleotide within one of the disclosed sequences, so long as the start site is capable of producing a polynucleotide of at least 19 base pairs. For example, an at least 19 contiguous base nucleotide sequence can comprise nucleotide 1 through nucleotide 19, nucleotide 2 through nucleotide 20, nucleotide 3 through nucleotide 21, and so forth to produce a 19mer. Thus, a 20mer can comprise nucleotide 1 through nucleotide 20, nucleotide 2 through nucleotide 21, nucleotide 3 through nucleotide 22, and so forth. Similar sequences above 20 contiguous nucleotides are envisioned.

By "dsRNA" or "dsRNA molecule" or "dsRNA effector molecule" or "double-stranded RNA effector molecule" is meant an at least partially double-stranded ribonucleic acid molecule containing a region of at least about 19 or more nucleotides that are in a double-stranded conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA) In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, desirably at least about 5, 6, 7, 9 to 15 nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (desirably linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide Effector Sequence, preferably 19 to 29, 19 to 27, or 19 to 21 nucleotides, which is a reverse complement to an opposite strand replication intermediate (anti-genomic RNA) of a single-stranded RNA virus, e.g., the anti-genomic minus strand of a plus strand RNA virus such as HCV, or the anti-genomic plus strand or non-mRNA plus strand sequences of a minus strand virus, and wherein the double-stranded RNA effector molecule directly targets said anti-genomic minus strand or said anti-genomic plus strand, respectively. In a preferred aspect said double-stranded RNA effector molecules are provided by providing to the vertebrate cell an expression construct encoding the double-stranded RNA effector molecules.

In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other. In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. Desirably, the regions of complementarity are at least 70, 80, 90, 95, 98, or 100% complementary. Desirably, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a target viral RNA or target cDNA being represented in the dsRNA. In some embodiments, the dsRNA does not contain any single-stranded regions, such as single-stranded ends, or the dsRNA is a hairpin, comprising self-complementary regions which assume a double-stranded "stem" conformation separated by a single-stranded "loop" region. In other embodiments, the dsRNA has one or more single-stranded regions at various positions within the dsRNA molecule and/or including 3' and/or 5' overhangs of 1, 2, 3, 4, 5, 8, 10 or more nucleotides. Desirable RNA/DNA hybrids include a DNA strand or region that is an antisense strand or region (e.g., has at least 70, 80, 90, 95, 98, or 100% complementarity to a target nucleic acid) and an RNA strand or region that is a sense strand or region (e.g., has at least 70, 80, 90, 95, 98, or 100% identity to a target nucleic acid). In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999). Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999. In other embodiments, the dsRNA contains coding sequences or non-coding sequences, for example, a regulatory sequence (e.g., a transcription factor binding site, a promoter, or a 5' or 3' UTR of an mRNA) or, as in the invention, RNA sequences of the non-coding strand of a viral genome. Additionally, the dsRNA can be any of the at least partially dsRNA molecules disclosed in WO 00/63364, filed Apr. 19, 2000 (see, for example, pages 8-22), as well as any of the dsRNA molecules described in U.S. Provisional Application 60/399,998 filed Jul. 31, 2002, and PCT/US2003/024028, filed 31 Jul. 2003; and U.S. Provisional Application 60/419,532 filed Oct. 18, 2002, and PCT/US2003/033466, filed 20 Oct. 2003. Any of the dsRNAs may be expressed in vitro or in vivo using the methods described herein or standard methods, such as those described in WO 00/63364, filed Apr. 19, 2000 (see, for example, pages 16-22).

dsRNA "hairpin" constructs encoding a unimolecular hairpin dsRNA are more desirable for some applications than constructs encoding duplex dsRNA (i.e., dsRNA composed of one RNA molecule with a sense region and a separate RNA molecule with an antisense region) because the single-stranded RNA with inverted repeat sequences more efficiently forms a dsRNA hairpin structure, particularly where a dsRNA molecule is transcribed from an expression construct encoding the dsRNA, including where a dsRNA is supplied to a vertebrate cell by transfecting into the cell an expression construct encoding the dsRNA. This greater efficiency is due in part to the occurrence of transcriptional interference arising in vectors containing converging promoters that generate duplex dsRNA. Transcriptional interference results in the incomplete synthesis of each RNA strand thereby reducing the number of complete sense and antisense strands that can base-pair with each other and form duplexes. Transcriptional interference can be overcome, if desired, through the use of (i) a two vector system in which one vector encodes the sense RNA and the second vector encodes the antisense RNA, (ii) a bicistronic vector in which the individual strands are encoded by the same plasmid but through the use of separate cistrons, or (iii) a single promoter vector that encodes a hairpin dsRNA, i.e., an RNA in which the sense and antisense sequences are encoded within the same RNA molecule. Hairpin-expressing vectors have some advantages relative to the duplex vectors. For example, in vectors that encode a duplex RNA, the RNA strands need to find and base-pair with their complementary counterparts soon after transcription. If this hybridization does not happen, the individual RNA strands diffuse away from the transcription template and the local concentration of sense strands with respect to antisense strands is decreased. This effect is greater for RNA that is transcribed intracellularly compared to RNA transcribed in vitro due to the lower levels of template per cell. Moreover, RNA folds by nearest neighbor rules, resulting in RNA molecules that are folded co-transcriptionally (i.e., folded as they are transcribed). Some percentage of completed RNA transcripts is therefore unavailable for base-pairing with a complementary second RNA because of intra-molecular base-pairing in these molecules. The percentage of such unavailable molecules increases with time following their transcription. These molecules may never form a duplex because they are already in a stably folded structure. In a hairpin RNA, an RNA sequence is always in dose physical proximity to its complementary RNA. Since RNA structure is not static, as the RNA transiently unfolds, its complementary sequence is immediately available and can participate in base-pairing because it is so close. Once formed, the hairpin structure is predicted to be more stable than the original non-hairpin structure. Especially desirable are, e.g., "forced" hairpin constructs, partial hairpins capable of being extended by RNA-dependent RNA polymerase to form dsRNA hairpins, as taught in U.S. Ser. No. 60/399,998P, filed 31 Jul. 2002; and PCT/US2003/024028, "Double Stranded RNA Structures and Constructs and Methods for Generating and Using the Same," filed 31 Jul. 2003; as well as the "udderly" structured hairpins, hairpins with mismatched regions, and multi-epitope constructs as taught in U.S. Ser. No. 60/419, 532, filed 18 Oct. 2002, and PCT/US2003/033466, "Double-Stranded RNA Structures and Constructs, and Methods for Generating and Using the Same," filed 20 Oct. 2003. The latter applications in particular provide methods and compositions that are especially valuable for expressing one or more, including multiple short hairpin dsRNA molecules, each of which can be designed to target a selected viral strand, e.g., the minus strand of the positive-strand HCV, using the principles and methods as taught herein. In some aspects the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), preferably less than 100 to 200 nt, in which at least one stretch of at least 15 to 100 nucleotides (preferably 17 to 50 nt, more preferably 19 to 29 nt) is based paired with a complementary sequence located on the same RNA molecule (single RNA strand), and where said sequence and complementary sequence are separated by an unpaired region of at least about 4 to 7 nucleotides (preferably about 9 to about 15 nucleotides) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, preferably about 9 to about 15 nucleotides, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence; e.g., if the selected Effector Sequence and Effector Complement are long enough, they will form a double-stranded stem region at least 19-21 nt in length separated by 3 or 4 nucleotides which steric constraints force into an unpaired "loop". Included shRNAs are dual or bi-finger and multi-finger hairpin dsRNAs, in which the RNA molecule comprises two or more of such stem-loop structures separated by a single-stranded spacer region. In one aspect, the invention provides vector compositions comprising a plurality of RNA Polymerase III promoters, preferably human or mammalian RNA polymerase III promoters, which control the expression of multiple shRNA molecules with homology to RNA sequences from viruses causing human disease, e.g., single stranded RNA viruses as described herein. The plurality of RNA polymerase III promoters may be the same or different. The invention provides the means of delivering to a host cell therapeutic and sustained amounts of 2, 3, 4, 5, or more different antiviral dsRNA hairpin molecules, in a genetically stable mode, which inhibits viral replication using 2, 3, 4, 5, or more independent viral sequence elements without evoking a dsRNA stress response. In one aspect, each RNA polymerase III promoter sequence is operably linked to a sequence encoding a different dsRNA hairpin molecule. Advantageously, three, four, five, six or more dsRNA effector molecules, e.g., hairpin dsRNA, including at least one, two, three or more antiviral opposite-strand replication intermediate targeting dsRNA effector molecules (e.g., targeting the HCV minus or anti-genomic strand), are administered, either alone or in combination with one, two, three, four, five, six or more antiviral dsRNA effector molecules (e.g., dsRNA hairpins) targeting the genomic RNA strand (e.g., targeting the HCV plus or genomic strand RNA).

In one aspect, one or more polymerase III promoters expresses an RNA transcript which forms a bi-fingered or dual dsRNA hairpin molecule comprising two or more shRNAs of the invention (each comprising a stem-loop structure) separated by a single-stranded region. The two or more shRNAs may target the same or different sequences of the same or different strands of the same virus or of different viruses.

In one aspect the regions of self-complementarity of the hairpin dsRNA or the double-stranded region of a duplex dsRNA will comprise an Effector Sequence and an Effector Complement (desirably linked by a single-stranded loop region in a hairpin dsRNA). The Effector Sequence or Effector Strand is that strand of the double-stranded region or duplex which is incorporated in or associates with RISC.

By "expression vector" is meant any vector which comprises elements such as, e.g., a promoter, used to transcribe an RNA, e.g., a vector that contains at least one promoter operably linked to a downstream gene or a coding or non-coding region of interest (e.g., a cDNA or genomic DNA fragment that encodes a protein, or any RNA of interest, e.g., sequences encoding viral genomic strand RNA or anti-genomic strand RNA, coding and/or non-coding sequences as described herein, optionally, e.g., operatively linked to sequence lying outside a coding region, an antisense RNA coding region, a dsRNA coding region, or RNA sequences lying outside a coding region). An "expression construct" as used herein means any expression vector comprising the sequence coding for a dsRNA effector molecule operably linked to elements, e.g., a promoter, used in the expression of the dsRNA effector molecule. Transfection or transformation of the expression construct into a recipient cell allows the cell to express dsRNA encoded by the expression construct. An expression construct may be a genetically engineered plasmid, virus, or artificial chromosome derived from, for example, a bacteriophage, adenovirus, retrovirus, poxvirus, or herpesvirus. An expression construct does not have to be replicable in a living cell, but may be made synthetically. Preferred expression vectors for expression of double-stranded RNAs, including dsRNA hairpin molecules, are described in U.S. Provisional Application 60/497,304, WO 2005/040388, pub. 6 May 2005 and in US/PCT2004/026999 "Multiple Compartment Eukaryotic Expression Systems" and in US Provisional Applications 60/362,260 and 60/629,942, filed 23 Aug. 2004 and 22 Nov. 2004, respectively, and in PCT/US2005/29978, filed 23 Aug. 2005, "Multiple RNA Polymerase III Promoter Expression Constructs". The term "in vivo" is intended to include any system wherein the cellular DNA or RNA replication machinery is intact, including tissue culture systems, and within single cells, tissues, organs, or multicellular living organisms.

By "infection", "infected", "viral infection", or "virally infected" is meant the invasion of a host organism, host tissue(s), or host cell(s) by a virus. For example, the infection may include the excessive growth of viruses that are normally present in or on the body of an animal or growth of viruses that are not normally present in or on the animal. More generally, a viral infection can be any situation in which the presence of a viral population(s) is damaging to a host organism. Thus, an organism is "suffering" from a viral infection when an excessive amount of a viral population is present in or on the organism, or when the presence of a viral population(s) is damaging the cells or other tissue of the organism.

The viral infection relevant to the methods of the invention is an infection by one or more of the following viruses which are members of the group of single-stranded RNA viruses of plus strand or minus strand classes. The plus-stranded viruses include the human coronaviruses (exemplified by the agent which causes severe acute respiratory syndrome (SARS)); flaviviruses including West Nile encephalitis virus (VNV), Japanese encephalitis (JE) virus, Murray Valley encephalitis (MVE) virus, St. Louis encephalitis virus, yellow fever virus, hepatitis C virus (HCV); Dengue fever virus, Rubella virus, caliciviruses such as Norwalk virus, hepatitis E virus, poliovirus, rhinovirus, hepatitis A virus, coxsakie virus, Venezuelan equine encephalitis virus, and foot-and-mouth-disease virus (FMDV). The minus strand viruses include influenza virus, Ebola and Marburg viruses, respiratory syncitial virus, parainfluenza virus, measles virus, mumps virus, rabies virus, and vesicular stomatitis virus (VSV). Another class of single-stranded RNA viruses known as ambisense viruses is exemplified by Lassa fever virus and hantavirus (hemorrhagic fever viruses). Infection by the above viruses can occur via several routes of transmission, via a preferred route for some or via multiple routes for others. Infection can occur when a bodily fluid (e.g., blood, saliva, or mucus) of an infected individual is ingested or inhaled by, or introduced into another individual by penetration of the skin or mucosal surface (e.g., vagina, nasal cavity, or mouth). Thus, some of these viruses can be transmitted by direct contact with infected individuals or through inhalation of aerosolized virus particles. Additionally, some of these viruses retain structural integrity and infectious properties in the environment, such as on common surfaces, foodstuffs, etc. and may be transmitted through indirect contact, whereas others require direct contact with an infected individual or organism. Some of these viruses may be transmitted from non-human species, such as mosquitoes or rodents, directly to humans while others cannot.

Methods disclosed herein can be used to treat subjects already infected with a virus in order to shut down or inhibit viral replication. Further, methods disclosed herein can be employed in a prophylactic mode if a pharmaceutical formulation of this invention is administered prior to initial infection. Treatment of chronic infection such as HCV is a particularly useful method of the invention. A dsRNA expression construct which continues to provide one or more, preferably a multiplicity of dsRNA effector molecules to a cell over an extended period of time is especially desirable for prophylactic applications and chronic infections. By "modulates" is meant changing, either by a decrease or an increase. As used herein, desirably a dsRNA effector molecule decreases viral replication in a cell by least 20%, more desirably by at least 30%, 40%, 50%, 60% or 75%, and most desirably by at least 90% as compared to normal replication levels of the target virus as measured by one or more indirect assays for viral replication. The dsRNA effector molecules of the invention which target the "opposite" strand replication intermediate (anti-genomic strand) of a single-stranded RNA virus, i.e., the minus strand replication intermediate of a plus strand RNA virus such as, for example, HCV or plus strand polarity non-mRNA segments of a minus strand RNA virus, desirably decrease viral replication by at least 20%, more desirably by at least 30%, 40%, 50%, 60%, 75%, and most desirably by at least 90%, 95%, or 100%, as compared to the decrease in viral replication levels achieved using an equivalent dsRNA effector molecule directed to the more abundant strand.

In some aspects, the opposite-strand targeting dsRNA molecule (e.g., the HCV minus strand targeting dsRNA) will directly decrease levels of the anti-genomic RNA strand but will have no direct effect on levels of the genomic RNA strand (e.g., the HCV genomic RNA strand) of the virus (although there can be an indirect effect because decreasing levels of the anti-genomic strand template will result in reduced levels of the genomic RNA strand which is made from the template). In some aspects of the invention, the opposite-strand targeting dsRNA molecule will directly decrease levels of the anti-genomic RNA strand and to a lesser extent may also directly decrease levels of the genomic RNA strand. An effective opposite-strand targeting dsRNA molecule comprises an Effector Sequence which preferentially associates with RISC relative to its Effector Complement; by an Effector Sequence which "preferentially" associates with RISC is meant a nucleic acid sequence which associates with RISC to an extent greater than 50%, 60%, 70%, 80%, 90% relative to the other strand. As a result, levels of the targeted RNA strand will be decreased. This decrease in levels of "opposite" strand replication intermediate (anti-genomic strand) of a single-stranded RNA virus is independent or direct and not secondary to decreases in the more abundant or genomic RNA strand which may result from some Effector Complement sequences being loaded on RISC. It has been reported that siRNA molecules targeted to structural (E2) and non-structural genes (NS3 and NS5B) of HCV reduced expression of HCV core and NS5A proteins as well as inhibiting synthesis of the replicative negative strand HCV RNA, Prabhu et al., J. Med. Virol. 76(4):511-9 (2005). This is not unexpected in that RNAi-mediated degradation of the HCV coding strand (the HCV genomic RNA), which serves as the template for synthesis of the negative strand or anti-genomic RNA, would be expected to result in a secondary or indirect decrease in levels of the negative strand. In contrast, the opposite-strand targeting dsRNA molecules of the invention (e.g., the HCV minus strand targeting dsRNAs) will directly decrease levels of the anti-genomic RNA strand through RNAi, independent of any decreases secondary to effects on the genomic or abundant RNA strand.

In some applications one, two, three, four or more dsRNA effector molecules of the invention which target the "opposite" strand replication intermediate (the anti-genome strand) of a virus are provided to a cell together with one, two, three, four or more dsRNA effector molecules which target the viral genomic RNA strand, in order to achieve a decrease in viral replication of at least 30%, 40%, 50%, 60%, 75%, and most desirably by at least 90%, 95%, or 100%, as compared to normal replication levels of the target virus as measured by one or more indirect assays for viral replication. These assays may include Northern Blotting, which typically can measure the levels of minus strand and/or plus strand viral RNA present in the infected cells. The RNA strands can also be quantified with high sensitivity and accuracy using a PCR (polymerase chain reaction) assay in addition or instead of Northern Blotting. Viral replication is also typically measured using a "plaque assay", in which the infected cells in question are processed for harvesting of viral particles, and the number of functional viral particles recovered is measured by infecting another set of cells and counting viral plaques formed in the cell culture plate. See also "Methods and Constructs for Evaluation of RNAi Targets and Effector Molecules", WO 2004/076629, published 10 Sep. 2004, the teaching of which is incorporated herein by reference. Although achieving HCV viral replication in tissue culture has been problematical, HCV replicon systems suitable for studying HCV replication and assessing anti-HCV activity are now available, see e.g., Pietschmann et al., 2002, *J. Virol.* 76:4008-4021; Zhong et al., Proc. Natl. Acad. Sci. USA 102 (26):9294-99 (2005); see also Apath, LLC, St. Louis, Mo.

By "multiple sequitope dsRNA" or "multisequitope dsRNA" is meant an RNA molecule that has segments derived from multiple target nucleic acids or that has non-contiguous segments from the same target nucleic acid. For example, the multiple sequitope dsRNA may have segments derived from (i) sequences representing multiple genes of a single organism, e.g., multiple genes from the same target pathogen; (ii) sequences representing one or more genes from a variety of different organisms; and/or (iii) sequences representing different regions of a particular gene (e.g., one or more sequences from a promoter and/or other regulatory region and one or more sequences from an mRNA). Desirably, each segment has substantial sequence identity to the corresponding region of a target nucleic acid. In various desirable embodiments, a segment with substantial sequence identity to the target nucleic acid is at least 19, 20, 21, 22, 23, 24, 25, 26, 27, 28, 29, 30, 40, 50, 100, 200, 500, 750, or more basepairs in length, desirably between 19 and 30, 19 and 27, or between 19 and 25, Inclusive, basepairs in length. In some embodiments, the multiple epitope dsRNA has non-contiguous segments from the same target gene that may or may not be in the naturally occurring 5' to 3' order of the segments, and the dsRNA inhibits replication by at least 25, 50, 100, 200, 500, or 1000% more than a dsRNA with only one of the segments.

The advantages of a multiple-epitope or multisequitope double-stranded RNA approach as taught in U.S. Ser. No. 60/419,532, filed 18 Oct. 2002 and PCT/US2003/033466, filed 20 Oct. 2003, are applicable to utilization of the conserved sequences of the invention. Because a singular species of dsRNA can simultaneously silence many target genes (e.g., genes from multiple pathogens, multiple genes or sequences from a single pathogen, or genes associated with multiple diseases), a multiple epitope dsRNA can be used for many different indications in the same subject or used for a subset of indications in one subject and another subset of indications in another subject. For such applications, the ability to express long dsRNA molecules (e.g., dsRNA molecules with sequences from multiple games) without invoking the dsRNA stress response is highly desirable. For example, by using a series of sequences, each, e.g., as short as 19-21 nucleotides, desirably 100 to 600 nucleotides, or easily up to 1, 2, 3, 4, 5, or more kilobases such that the total length of such sequences is within the maximum capacity of the selected plasmid (e.g., 20 kilobases in length), a single such pharmaceutical composition can provide protection against a large number of pathogens and/or toxins at a relatively low cost and low toxicity.

The ability to silence multiple genes of a particular pathogen prevents the genetic selection of "escape mutants." In contrast, typical small molecule treatment or immunotherapy that only targets one g ene or protein results in the selection of pathogens that have sustained mutations in the target gene or protein and the pathogen thus becomes resistant to the therapy. By simultaneously targeting a number of genes or sequences of the pathogen and or extensive regions of the pathogen using the multiple epitope approach of the present invention, the emergence of such "escape mutants" is effectively precluded. The dsRNA molecules of the invention, designed to target opposite-strand viral RNAs such as the HCV negative strand anti-genomic RNA, provide a new set of targets and a new set of antiviral molecules to be used alone and in concert with dsRNAs targeting viral genomic RNA, as well as with other antiviral agents. In preferred embodiments, conserved regions of the viral RNAs will be targeted. For example, in one aspect it may be desirable to provide to a human cell or organism infected with HCV a multiplicity of dsRNA molecules, including one or more dsRNA molecules targeting conserved sequences of the HCV anti-genomic negative strand, and in some embodiments, one or more additional dsRNA molecules targeting conserved sequences of the genomic plus strand RNA, including both coding sequences and non-coding sequences, e.g., the 5' UTR (IRES), Core, NS3, NS4B, NS5A, NS5B, and the 3' UTR. In one aspect, a multiplicity of dsRNA molecules are used, selected from the group consisting of: one or more dsRNAs targeted to one or more conserved sequences of the HCV 5' UTR (−) strand; one or more dsRNAs targeted to one or more conserved sequences of the 5' UTR (+) strand; one or more dsRNAs targeted to one or more conserved sequences of the 3' UTR (−) strand; one or more dsRNAs targeted to one or more conserved sequences of the 3' UTR (+) strand; and optionally, one or more dsRNAs targeting HCV (+) core, NS3, NS4B, NS5A, and/or NS5B sequences; and, optionally, one or more other antiviral molecules active against HCV, such as, e.g., interferon alfa-2a+ribavirin; peginterferon alfa-2b, etc.

Whether such a multiplicity of dsRNAs is delivered as a "cocktail" of exogenously synthesized, optionally chemically modified dsRNAs, or supplied to a vertebrate cell, tissue or organism via one or more expression vectors encoding such dsRNA molecules, e.g., one or more multiple polymerase III promoter expression constructs, the availability of such a variety of antiviral agents is critical to the design of effective antiviral therapeutics, due to the nature of viral variation both within human populations and temporally within a host due to mutation events. For example, this aspect of the invention provides a means for delivering a multi-drug regimen comprising several different dsRNA viral inhibitor molecules to a cell or tissue of a host vertebrate organism, such that the level of viral inhibition is potentiated and the probability of multiple independent mutational events arising in the virus and rendering dsRNA inhibition of viral replication ineffective, would be infinitesimally small. This ability to supply a multi-drug regimen, e.g., multi-dsRNA regimen, is especially critical for RNA viruses, with their extremely high mutation rate.

By "nucleic acid composition" or "nucleotide" composition is meant any one or more compounds in which one or more molecules of phosphoric acid are combined with a carbohydrate (e.g., pentose or hexose) which are in turn combined with bases derived from purine (e.g., adenine) and from pyrimidine (e.g., thymine). Particular naturally occurring nucleic acid molecules include genomic deoxyribonucleic acid (DNA) and host ribonucleic acid (RNA), as well as the several different forms of the latter, e.g., messenger RNA (mRNA), transfer RNA (tRNA), and ribosomal RNA (rRNA). Also included are different DNA molecules which are complementary (cDNA) to the different RNA molecules. Synthesized DNA or a hybrid thereof with naturally occurring DNA, as well as DNA/RNA hybrids, and peptide nucleic acid (PNA) molecules (Gambari, Curr. Pharm. Des. 7:1839-62 (2001)) can also be used.

It is contemplated that where the desired nucleic acid molecule is RNA, the T (thymine) in the sequences provided herein is substituted with U (uracil). For example, SEQ ID NO:1 through SEQ ID NO:59 are disclosed herein as DNA sequences. It will be obvious to one of ordinary skill in the art that an RNA effector molecule comprising sequences from any of the aforementioned SEQ ID NOs will have T substituted with U. Nucleic acids typically have a sequence of two or more covalently bonded, naturally-occurring or modified deoxyribonucleotides or ribonucleotides. Modified nucleic acids include, e.g., peptide nucleic acids, nucleotides with unnatural bases, and chemically modified bases.

The term "operably linked" refers to a functional linkage between a nucleic acid expression control sequence (such as a promoter, signal sequence, enhancer or array of transcription factor binding sites) and a second nucleic acid sequence, wherein the expression control sequence affects transcription and/or translation of the nucleic acid corresponding to the second sequence when the appropriate molecules (e.g., transcriptional activator proteins) are bound to the expression control sequence. An expression construct encoding a dsRNA molecule of the invention will include a promoter operably linked to a nucleic acid sequence to be transcribed, e.g., a sequence encoding a hairpin dsRNA molecule or one strand of a duplex dsRNA, In one aspect, dsRNA expression constructs comprising two, three, four or more RNA polymerase III promoters, may comprise a nucleic acid sequence encoding an shRNA or dsRNA hairpin of the invention operably linked to one, two, three, four or to each of said promoters.

"Opposite strand replication intermediate" or "anti-genomic RNA" as used herein, means the minus strand RNA complement of a plus strand virus or non-mRNA sequences of the plus strand RNA complement of a minus strand virus. For Example, HCV is a plus strand virus having a plus strand (sense) genomic RNA which during replication serves as a template for transcription of the anti-genomic negative strand RNA (i.e., the opposite strand replication intermediate). As disclosed herein, a dsRNA effector molecule comprises a reverse complement of a single-stranded virus' opposite strand replication intermediate. Thus, for example, a plus strand virus comprising the nucleic acid sequence ATAGCT would have an opposite strand replication intermediate comprising the nucleic acid sequence TATCGA (read in the 3' to 5' direction, i.e., the complement of the plus strand). A dsRNA effector molecule targeting this sequence on the opposite strand replication intermediate would thus comprise a reverse complement of the opposite strand replication intermediate, i.e., the nucleic acid sequence ATAGCT (read in the 5' to 3' direction). This reverse complement sequence which targets the desired replication intermediate is the Effector Sequence, and dsRNA effector molecules of the invention are designed to ensure that the Effector Sequence (as opposed to its Effector Complement) preferentially associates with the RNA induced silencing complex (RISC) to mediate RNAi. In some preferred embodiments of the invention, the dsRNA effector molecules of the invention are designed to target the minus strand replication intermediate of a plus strand virus, e.g., HCV.

By a "promoter" is meant a nucleic acid sequence sufficient to direct transcription of an operably linked nucleic acid molecule. Also included in this definition are those transcription control elements (e.g., enhancers) that are sufficient to render promoter-dependent gene expression controllable in a cell type-specific, tissue-specific, or temporal-specific manner, or that are inducible by external signals or agents; such elements, which are well-known to skilled artisans, may be found in a 5' or 3' region of a gene or within an intron. Desirably, a promoter is operably linked to a nucleic acid sequence, for example, a cDNA or a gene in such a way as to permit expression of the nucleic acid sequence. Especially desirable in some embodiments for expression of the dsRNA effector molecules of the invention are the promoters, multiple-compartment expression systems and multiple-compartment promoter systems as taught in "Multiple-Compartment Eukaryotic Expression Systems", PCT/US04/26999, filed Aug. 20, 2004, and in U.S. Provisional Application 60/497,304, filed Aug. 22, 2003, as well as the promoters and multiple polymerase III promoter expression constructs taught in U.S. Provisional Applications 60/603,622 filed 23 Aug. 2004; 60/629,942 filed 22 Nov. 2004; and in PCT/US2005/29976 filed 23 Aug. 2005.

An "RNA effector molecule" as used herein comprises a ribonucleic acid sequence comprising at least 19 contiguous nucleotides homologous to the reverse complement of the opposite strand replication intermediate of a single-stranded RNA virus. Said at least 19 contiguous nucleotides homologous to the reverse complement of the opposite strand replication intermediate of a single-stranded virus will be present in a double-stranded conformation. An RNA effector molecule of the invention can be, for example, a dsRNA duplex comprising two separate strands, or a single RNA strand comprising self complementary regions which are capable of assuming a stem-loop or hairpin conformation. More particularly, in order to target the desired viral anti-genomic RNA strand (i.e., the opposite strand replication intermediate), the reverse complement sequence of the viral target (i.e., the Effector Strand or Effector Sequence)) will be present in the cell (as provided to the cell, expressed in the cell, or after being cleaved by cellular nucleases) as part of a dsRNA duplex of between 19-27 or 19-29 nucleotides, inclusive, i.e., 19, 20, 21, 22, 23, 24, 25, 26, 27, 28, or 29 nucleotides, preferably 19, 20, or 21 nucleotides, present in double-stranded conformation and said Effector Strand will be selected so that its 5' terminus will be part of a duplex with a lower internal stability (see Khvorova et al., Cell 115:209-16 (2003)) as compared to its 3' terminus. This will increase the likelihood that the Effector Strand of the dsRNA will associate functionally with the RISC complex which mediates RNAi.

By "sequitope" is meant a contiguous sequence of double-stranded polyribonucleotides that can associate with and activate RISC(RNA-induced silencing complex), usually a contiguous sequence of between 19 and 27 or 29 basepairs, inclusive. Such a double-stranded sequitope will comprise an Effector Sequence and its reverse complement, the Effector Complement. It is desirable to select a sequitope which will target the minus strand replication intermediate (i.e., the anti-genomic RNA strand) of a plus strand single-stranded RNA virus such as HCV, and conversely, will target the plus strand (anti-genomic RNA strand) of a minus strand single stranded RNA virus. This may be accomplished through any of a variety of means which increases the association of the Effector Strand with the RISC complex, relative to the Effector Complement.

"Single-stranded virus" or "single-stranded RNA virus", as used herein, means a virus having a genome of either plus strand RNA or minus strand RNA. "Plus strand" means RNA having the same polarity as the corresponding viral mRNA or the RNA which encodes the viral proteins. Non-limiting examples of plus strand RNA viruses include human coronavirus (SARS agent), West Nile Encephalitis virus (WNV), hepatitis C virus (HCV), Dengue fever virus, Norwalk virus, poliovirus, rhinovirus, hepatitis A and hepatitis E virus, Venezuelan equine encephalitis virus, Japanese encephalitis virus (JE), Rubella virus, coxsackie virus, and foot-and-mouth-disease virus (FMDV). "Minus strand" means RNA having the opposite polarity as the corresponding viral mRNA which encodes the viral proteins. Non-limiting examples of minus strand RNA viruses include influenza virus, Ebola virus, Marburg virus, respiratory syncitial virus, parainfluenza virus (PIV), measles virus, mumps virus, rabies virus, and vesicular stomatitis virus (VSV).

By "substantial sequence complementarity" is meant sufficient sequence complementarity between a dsRNA, or other biologically active nucleic acid, and a target nucleic acid molecule for the nucleic acid to inhibit the expression of the target nucleic acid molecule. Preferably, the sequence of the dsRNA is at least 40, 50, 60, 70, 80, 90, 95, or 100% complementary to the sequence of a region of the target nucleic acid molecule. For purposes of providing a dsRNA effector molecule of the invention, there will desirably be a minimum of 19 or 20 contiguous nucleotides (the "Effector Sequence") having 100% complementarity (i.e., the reverse complement) to the target viral sequence, i.e., 100% complementarity to a sequence of 19-27, 28, or 29 nucleotides of the target viral replication intermediate RNA (anti-genomic RNA strand), e.g., complementarity to a sequence of the HCV minus strand replication intermediate. In contrast to the 100% sequence complementarity required of this "Effector Sequence", however, the other strand of the dsRNA effector molecule (the "Effector Complement") may be completely complementary to the Effector Sequence or it may include a minimum number of mismatched nucleotides, e.g., one, two, or three mismatched nucleotides may be present in the 3' terminal region of the "Effector Complement" which hybridizes with the 5' terminal region of the "Effector Sequence", so long as the desired terminus itself remains in a double stranded conformation.

By "substantial sequence identity" is meant sufficient sequence identity between a dsRNA or antisense RNA and a target nucleic acid molecule for the dsRNA or antisense molecule to inhibit the expression of the target nucleic acid molecule. Preferably, the sequence of the dsRNA or antisense RNA is at least 40, 50, 60, 70, 80, 90, 95, or 100% identical to the sequence of a region of the target nucleic acid molecule, and in a dsRNA molecule, will preferably include a sequence of about 19 to about 25, 26, 27, 28, or 29 nucleotides of complete sequence identity relative to a target. In a preferred embodiment, this sequence identity will be present (as the reverse complement) in the "Effector Sequence" strand of a dsRNA effector molecule of the invention.

Another indication that nucleotide sequences are substantially identical is if two molecules hybridize to each other under stringent conditions. Stringent conditions are sequence-dependent and will be different in different circumstances. Generally, stringent conditions are selected to be about 5° C. to about 20° C., usually about 10° C. to about 15° C., lower than the thermal melting point for the specific sequence at a defined ionic strength and pH. The thermal melting point is the temperature (under defined ionic strength and pH) at which 50% of the target sequence, i.e., the opposite strand replication intermediate, hybridizes to a perfectly matched probe. Typically, stringent conditions will be those in which the salt concentration is about 0.02 molar at pH 7.0 and the temperature is at least about 60° C. For instance in a standard Southern hybridization procedure, stringent conditions will include an initial wash in 6×SSC at 42° C. followed by one or more additional washes in 0.2×SSC at a temperature of at least about 55° C., typically about 60° C. and often about 65° C.

By "treating, stabilizing, or preventing a viral infection" is meant preventing or delaying an initial or subsequent occurrence of a viral infection; increasing the disease-free survival time between the disappearance of a viral infection and its reoccurrence; stabilizing or reducing an adverse symptom associated with a viral infection; or inhibiting or stabilizing the progression of a viral infection. This includes prophylactic treatment, in which treatment before infection with an infectious agent is established prevents or reduces the severity or duration of infection. Preferably, at least 20, 40, 60, 80, 90, or 95% of the treated subjects have a complete remission in which all evidence of the viral infection disappears, at least for a period of time. In another aspect, treatment will result in a clinically relevant reduction in at least some signs or symptoms of an ongoing viral infection, e.g., a significant reduction in viral load, a significant reduction in hepatic enzymes associated with viral disease, or an improvement in function correlating to a modulation of disease. In another embodiment, the length of time a patient survives after being diagnosed with a viral infection and treated using a method of the invention is at least 20, 40, 60, 80, 100, 200, or even 500% greater than (i) the average amount of time an untreated patient survives, or (ii) the average amount of time a patient treated with another therapy survives. The terms "nontranslated region" ("NTR") and "untranslated region" ("UTR") are used interchangeably herein and refer to nucleic acid sequences which are not coding sequences, e.g., sequences of an mRNA 5' to the translation initiation (ATG) site and 3' to the translation stop site, which are not translated to make a peptide.

In any aspect of the invention, an infected or target cell can be a vertebrate cell. Desirably the vertebrate cell is a mammalian cell, preferably a human cell. The cell may be ex two or in vivo. The cell may be a gamete or a somatic cell, for example, a cancer cell, a stem cell, a cell of the immune system, a neuronal cell, a muscle cell, or an adipocyte. In some embodiments, one or more proteins involved in gene silencing, such as Dicer or Argonaut, are overexpressed or activated in the cell or animal to increase the amount of inhibition of gene expression. Preferably, the cell is a mammalian cell, more preferably a human cell. A "target cell" includes uninfected cells. Thus, a target cell can be a cell wherein prevention of viral infection is sought. When such a target cell comprises dsRNA effector molecules as disclosed herein, dsRNA effector molecules in such cells can target opposite strand replication intermediates when these cells become infected with the corresponding single-stranded virus.

It has been discovered that, surprisingly, it is desirable to design nucleic acid-based antiviral molecules to target the opposite strand replication intermediate of a plus strand virus such as HCV, and the non-mRNA sequences of the anti-genomic plus strand of minus strand viruses, as well as the minus strand of minus strand viruses. dsRNA effector molecules may be designed to target the minus strand replication intermediate through any means which preferentially increases the participation of the Effector Sequence in the RNAi process, e.g., by increasing the affinity, association, or "loading" of the Effector Strand of such a dsRNA with or to the RISC mediator of RNAi. One such method designed to target the opposite strand replication intermediate of a single-stranded virus is based on a simplification of rules and observations described by Reynolds at al., Nature Biotechnol. 22:326-30 (2004); Schwartz et al., Cell 115:199-208 (2003); and Khvorova et al., Cell 115:209-16 (2003). Also Amarzguioui and Prydz, "An algorithm for selection of functional siRNA sequences", Biochem. Biophys. Res. Comm. 316: 1050-1058 (2004; and Ui-Tei et al., Nuc. Acids Res. 32:936-948 (2004). See also Technical Bulletin #506, "siRNA DesignGuidelines", Ambion, Inc., Austin, Tex. However, instead of selecting an mRNA (or plus strand genomic RNA) as the target for designing siRNA molecules as taught in the Ambion instructions, the target should be the anti-genomic RNA strand (i.e., the non-coding RNA strand) of a plus-strand single stranded RNA virus like HCV, rather than the plus strand itself. Similarly, the Dharmacon siDESIGN Center directs the user to "Identify Target mRNA Nucleotide Sequence" as the starting point for design of functional siRNA molecules, Dharmacon, Inc. Lafayette, Colo. By contrast, applicants have demonstrated superior results in targeting the anti-genomic RNA strand of single stranded RNA viruses, including the negative strand of HCV. Strand-specific targeting by dsRNA is based on the discovery that the sense strand and antisense strands present in a dsRNA molecule are not functionally equivalent in their ability to associate with and/or activate the mechanism of dsRNA-mediated gene silencing. Although it is believed that one strand from a dsRNA associates with or is "loaded" onto the silencing complex known as RISC, beginning with the strand's 5' end, each of the two strands present in a dsRNA will have a 5' and a 3' end, and each would therefore seem equally likely to be incorporated into the RISC. In actuality, however, it appears that the strand whose 5' end is present in a less thermally stable duplex will be more likely to be incorporated into the RISC. These principles can be utilized to design dsRNA effector molecules which preferentially target a selected strand of a virus, desirably the opposite strand replication intermediate of a single-stranded virus, e.g., the negative strand anti-genomic RNA of a plus-strand virus such as HCV.

A dsRNA effector molecule (a dsRNA molecule 19-27, or 19-29 nucleotides in length) will have two termini. For purposes of this application, a "terminus", "termini" or "end" means the terminal 2-6 basepairs, preferably 3-5 basepairs, at the ends of the duplex portion of a dsRNA. Because of differences in the nucleotide compositions of the two terminal sequences, however, it is unlikely that the two termini will have identical thermal stabilities. The terminus with the lower thermal stability will have a greater propensity to separate into its composite 3' and 5' ends. While not wishing to be bound by theory or mechanism, it is reasonable that an RNA strand whose 5' end is present in a duplex having a lower thermal stability relative to its 3' end will be more likely than its complement strand to be incorporated into the RISC complex. For example, Amarzguioui and Prydz, "An algorithm for selection of functional siRNA sequences", Biochem. Biophys. Res. Comm. 316:1050-1058 (2004), evaluated the number of A/U pairs in the terminal 3, 4, 5, and 6 nucleotides in both ends of an siRNA duplex, concluding that a positive (preferably +2 or +3, but at least not negative) A/U content differential between the terminal three nucleotides at the 5' and 3' ends (relative to the sense strand) of the duplex (ds) region was a superior predictor of functionality relative to a similar calculation relative to the terminal 7 basepairs as found in Ui-Tel et al., Nucleic Acids Res. 32:936-948 (2004). The presence or absence of overhangs was found to have little or no effect on activity, only the relative stability of the two termini of the duplex region. Design of a dsRNA according to these principles will result in a dsRNA molecule which targets an mRNA or a sense strand RNA such as the plus strand genomic RNA of HCV, because the analysis starts relative to an mRNA target sequence. In contrast, the Applicants have successfully adapted and utilized similar principles and considerations to target the negative strand replication intermediate (i.e., anti-genomic RNA strand) of the plus-strand hepatitis C virus, as described in greater detail below.

The ability to adapt and use these observations to achieve the desired viral strand targeting for enhanced RNAi has been confirmed by the Applicants in experimental permutations of dsRNA sequence variants. The specific criterion used to design strand-targeted dsRNAs in this invention is to require that the predicted thermal stability of the terminus comprising the 5' end of the Effector Strand (and the 3' end of the Effector Complement) needs to be lower than the thermal stability of the terminus comprising the 3' end of the Effector Strand (and the 5' end of the Effector Complement). In this context, 5' or 3' "end" or "terminus" means the terminal 3 to 5 base pairs. Predicted $T_m$ can be determined by application of a standard formula known to those skilled in the art, or by evaluating the relative number and position of weaker A-U bonds relative to stronger C-G bonds at the two termini of a dsRNA effector molecule. For example, a desirable 5' terminus of an Effector Strand would comprise a terminal A or U residue, while at least 2 of the next 4 residues should be either A or U. The 3' terminus of the Effector Strand would desirably terminate in G or C with at least 2 of the next 4 residues comprising either G or C. Alternatively, thermal stability can be estimated by free energy calculations using the methods of Khvorova of al. (Cell 115:209-16 (2003)) and references within.

In addition to delivery via intracellular expression from expression constructs as described below, the RNA effector molecule according to this invention may be delivered to the viral pathogen present in the mammalian cell as an RNA molecule or as a partially double-stranded RNA sequence, or RNA/DNA hybrid, which was made in vitro by conventional enzymatic synthetic methods using, for example, the bacteriophage T7, T3, or SP6 RNA polymerases according to the conventional methods described by such texts as the Promega Protocols and Applications Guide, (3rd ed. 1996), eds. Doyle, ISBN No. 1 57. Alternatively these molecules may be made by chemical synthetic methods in vitro [see, e.g., Q. Xu et al., Nucleic Acids Res. 24:3643-44 (1996); N. Naryshkin et al., Bioorg. Khim. 22:691-98 (1996); J. A. Grasby at al., Nucleic Acids Res. 21:444-450 (1993); C. Chaix et al., Nucleic Acids Res. 17:7381-93 (1989); S. H. Chou et al., Biochem. 28:2422-35 (1989); O. Odal et al., Nucleic Acids Symp. Ser. 21:105-06 (1989); N. A. Naryshkin et al., Bioorg. Khim. 22:691-98 (1996); S. Sun et al., RNA 3:1352-63 (1997); X. Zhang at al., Nucleic Acids Res. 25:3980-83 (1997); S. M. Grvaznov & H. Winter, Nucleic Acids Res. 26:4160-67 (1998); M. Kadokura at al., Nucleic Acids Symp. Ser. 37:77-78 (1997); A. Davison at al., Biomed. Pept. Proteins Nucleic Acids 2:1-6 (1996); and A. V. Mudrakovskaia et al., Bioorg. Khim. 17:819-22 (1991)].

Still alternatively, the RNA molecule of this invention can be made in a recombinant microorganism, e.g., bacteria and yeast or in a recombinant host cell, e.g., mammalian cells, isolated from the cultures thereof by conventional techniques, and then delivered to the host organism. See, e.g., the techniques described in Sambrook at al., MOLECULAR CLONING, A LABORATORY MANUAL, 2nd Ed.; Cold Spring Harbor Laboratory Press, Cold Spring Harbor, N.Y., 1989, which is exemplary of laboratory manuals that detail these techniques, and the techniques described in U.S. Pat. Nos. 5,824,538; 5,877,159; and 5,643,771.

Such RNA molecules prepared or synthesized in vitro may be directly delivered to the infected cell or to the infected organism as they are made in vitro. The references above provide one of skill in the art with the techniques necessary to produce any of the following specific embodiments, given the teachings provided herein. Therefore, in one embodiment, the "agents" or "dsRNA effector molecule" of the composition is a duplex (i.e., it is made up of two strands), either complete or partially double-stranded RNA. In another embodiment, the agent or "dsRNA effector molecule" of the composition may be a single-stranded RNA with self-complementary regions. Desirably the single-stranded RNA forms a hairpin at one or both termini. Desirably, the single-stranded RNA strand forms a hairpin at some intermediate portion between the termini. Such a single-stranded RNA strand may be designed to fold back upon itself to become partially double-stranded in vitro or in vivo. Yet another embodiment of an extant RNA molecule as the effective agent used in the compositions is a single-stranded RNA sequence comprising both a sense polynucleotide sequence and an antisense polynucleotide sequence, optionally separated by a non-base paired polynucleotide sequence. Preferably, this single-stranded RNA sequence has the ability to become double-stranded once it is in the cell, or in vitro during its synthesis.

Still another embodiment of this invention is an RNA/DNA hybrid as described above.

Still another embodiment of the synthetic RNA molecule is a circular RNA molecule that optionally forms a rod structure (see, e.g., K-S. Wang at, Nature 323:508-514 (1986)) or is partially double-stranded, and can be prepared according to the techniques described in S. Wang at al., Nucleic Acids Res. 22:2326-33 (1994); Y. Matsumoto et al., Proc. Natl. Acad. Sci. USA 87:7628-32 (1990); E. Ford & M. Ares, Proc. Natl. Acad. Sci. USA 91:3117-21 (1994); M. Tsagris et al., Nucleic Acids Res. 19:1605-12 (1991); S. Braun et al., Nucleic Acids Res. 24:4152-7 (1996); Z. Pasman at al., RNA 2:603-10 (1996); P. G. Zaphiropoulos, Proc. Natl. Acad. Sci. USA 93:6536-41 (1996); D. Beaudry at al., Nucleic Acids Res. 23:3064-6 (1995). Still another agent is a double-stranded molecule comprised of RNA and DNA present on separate strands, or interspersed on the same strand.

Desirably, the RNA effector molecule may be formed in vivo and thus delivered by a "delivery agent" which generates such a partially double-stranded RNA molecule in vivo after delivery of the agent to the infected cell or to the infected organism. Thus, the agent which forms the composition of this invention is, in one embodiment, a double-stranded DNA molecule "encoding" one of the above-described dsRNA effector molecules. The DNA agent provides the nucleotide sequence which is transcribed within the cell to become a double-stranded RNA. In another embodiment, the DNA sequence provides a deoxyribonucleotide sequence which within the cell is transcribed into the above-described single-stranded RNA sense or antisense strand, which optionally forms a hairpin at one or both termini or folds back upon itself to become partially double-stranded. The DNA molecule which is the delivery agent of the composition can provide a single-stranded RNA sequence comprising both an Effector Sequence and an Effector Complement, optionally separated by a linker or "loop" sequence, and wherein the self-complementary Effector Sequence and Effector Complement have the ability to assume a double-stranded "stem" conformation joined by a single-stranded "loop", i.e., a "hairpin" dsRNA. Alternatively, the DNA molecule which is the delivery agent provides for the transcription of the above-described circular RNA molecule comprising Effector Sequence and Effector Complement sequences that optionally forms a rod structure or partial double stranded structure in vivo. The DNA molecule may also provide for the in vivo production of an RNA/DNA hybrid as described above, or a duplex containing one RNA strand and one DNA strand. These various DNA molecules may be designed by resort to conventional techniques such as those described in Sambrook, cited above or in the Promega reference, cited above.

Another delivery agent of the present invention, which enables the formation in a cell of any of the above-described RNA molecules, can be a DNA single-stranded or double-stranded plasmid or vector. In some aspects a suitable recombinant viral vector, such as adenovirus or AAV, may be used to deliver an encoded dsRNA effector molecule of the invention. Expression vectors designed to produce RNAs as described herein in vitro or in vivo may contain sequences under the control of any RNA polymerase, including mitochondrial RNA polymerase, RNA pol I RNA pol II, and RNA pol III, and viral polymerases, and bacteriophage polymerases such as T7 and Sp6. Preferred for expression of oligonucleotides such as short hairpin dsRNAs or other dsRNA effector molecules less than about 300 to 400 nt in length are RNA polymerase III promoters. These vectors can be used to transcribe the desired RNA molecule in the cell according to this invention. Vectors may be desirably designed to utilize an endogenous mitochondrial RNA polymerase (e.g., human mitochondrial RNA polymerase, in which case such vectors may utilize the corresponding human mitochondrial promoter). Mitochondrial polymerases may be used to generate capped (through expression of a capping enzyme) or uncapped messages in vivo. RNA pol I, RNA pol II, and RNA pol III transcripts may also be generated in vivo. Such RNAs may be capped or not, and if desired, cytoplasmic capping may be accomplished by various means including use of a capping enzyme such as a vaccinia capping enzyme or an alphavirus capping enzyme. However, all pol II transcripts are capped. The DNA vector is designed to contain one of the promoters or multiple promoters in combination (mitochondrial, RNA pol I, pol II, or pol III, or viral, bacterial or bacteriophage promoters along with the cognate polymerases). Preferably, where the promoter is RNA pol II, the sequence encoding the RNA molecule has an open reading frame greater than about 300 nucleotides and must follow the rules of design to prevent nonsense-mediated degradation in the nucleus. Especially desirable in some embodiments for expression of the dsRNA effector molecules of the invention are the promoters, multiple-compartment expression systems and multiple-compartment promoter systems as taught in "Multiple-Compartment Eukaryotic Expression Systems", PCT/US04/26999, filed Aug. 20, 2004, and in U.S. Provisional Application 60/497,304, filed Aug. 22, 2003, and the RNA polymerase III promoters and multiple RNA polymerase III promoter expression constructs taught in U.S. Provisional Applications 60/603,622 filed 23 Aug. 2004; 60/629,942 filed 22 Nov. 2004; and in PCT/US2005/29976 filed 23 Aug. 2005.

Desirably, the methods, RNA structures, and expression constructs as taught in WO 04/035765 and PCT/US03/0033466, "Double-Stranded RNA Structures and Constructs and Methods for Generating and Using the Same", can be utilized to design and express the dsRNA effector molecules of the invention, comprising dsRNAs of 19-29, preferably 19-27 basepairs selected so that the Effector Sequence, complementary to and designed to target the replication intermediate RNA of a single-stranded RNA virus, is preferentially associated with the RISC. These methods and constructs may desirably be employed to express one or more, including a multiplicity of, siRNAs and/or shRNA (short hairpin RNAs) of the invention. Each of these siRNAs and/or shRNAs will be designed according to the principles described herein. See also the methods, RNA structures, and expression constructs taught in WO 04/011624 and PCT/US02/0399998, "Double-Stranded RNA Structures and Constructs and Methods for Generating and Using the Same".

Such plasmids or vectors can include plasmid sequences from bacteria, viruses, or phages. Such vectors include chromosomal, episomal, and virus-derived vectors, e.g., vectors derived from bacterial plasmids, bacteriophages, yeast episomes, yeast chromosomal elements, and viruses; vectors derived from combinations thereof, such as those derived from plasmid and bacteriophage genetic elements, cosmids and phagemids. Thus, one exemplary vector is a single- or double-stranded phage vector. Another exemplary vector is a single- or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally occurs only in complementing host cells.

In another embodiment, the delivery agent comprises more than a single DNA or RNA plasmid or vector. As one example, a first DNA plasmid can provide a single-stranded RNA polynucleotide comprising an Effector Sequence as described above, and a second DNA plasmid can provide a single-stranded RNA polynucleotide comprising an Effector Complement sequence as described above, wherein the RNA comprising the Effector Sequence and the RNA comprising the Effector Complement have the ability to base-pair and become double-stranded. Such plasmid(s) can comprise other conventional plasmid sequences, e.g., bacterial sequences such as the well-known sequences used to construct plasmids and vectors for recombinant expression of a protein. However, it is desirable that the sequences which enable protein expression, e.g., Kozak regions, etc., are not included in these plasmid structures. The vectors designed to produce dsRNAs of the invention may desirably be designed to generate two or more, including a number of different dsRNA effector molecules comprising sequences homologous and complementary to a target sequence. This approach is desirable in that a single vector may produce many, independently operative dsRNAs rather than a single dsRNA molecule from a single transcription unit and, by producing a multiplicity of different dsRNAs, it is possible to self select for optimum effectiveness. Various means may be employed to achieve this, including autocatalytic sequences as well as sequences for cleavage to create random and/or predetermined splice sites.

Other delivery agents for providing the information necessary for formation of the above-described desired RNA molecules in the infected cell include live or attenuated recombinant bacteria which are designed to contain the sequences necessary for the required RNA molecules of this invention. Such recombinant bacterial cells, fungal cells and the like can be prepared by using conventional techniques such as described in U.S. Pat. Nos. 5,824,538; 5,877,159; and 5,643,771. Microorganisms useful in preparing these delivery agents include those listed in the above cited references, including, without limitation, *Escherichia coli, Bacillus subtilis, Salmonella typhimurium*, and various species of *Pseudomonas, Streptomyces*, and *Staphylococcus*.

Still other delivery agents for providing the information necessary for formation of the desired, above-described RNA molecules in the mammalian cell include live, attenuated viruses, and particularly recombinant viruses carrying the required RNA polynucleotide sequence discussed above. Such viruses may be designed similarly to recombinant viruses presently used to deliver genes to cells for gene therapy and the like, but preferably do not have the ability to express a protein or functional fragment of a protein. Among useful viruses or viral sequences which may be manipulated to provide the required RNA molecule to the mammalian cell in vivo are, without limitation, alphavirus, adenovirus, adeno associated virus, baculoviruses, delta virus, pox viruses, hepatitis viruses, herpes viruses, papova viruses (such as SV40), poliovirus, pseudorabies viruses, retroviruses, lentiviruses, vaccinia viruses, positive and negative stranded RNA viruses, viroids, and virusoids, or portions thereof. These various viral delivery agents may be designed by applying conventional techniques such as described in M. Di Nocola et al., Cancer Gene Ther. 5:350-6 (1998), among others, with the teachings of the present invention.

Nucleic Acid Delivery

The dsRNA effector molecules of the invention and DNA and/or RNA constructs encoding the dsRNA effector molecules of the invention may be administered to the host cell/tissue/organism as "naked" DNA, RNA, or DNA/RNA, formulated in a pharmaceutical vehicle without any transfection promoting agent. More efficient delivery may be achieved as known to those of skill in the art of DNA and RNA delivery, using e.g., such polynucleotide transfection facilitating agents known to those of skill in the art of RNA and/or DNA delivery. The following are exemplary agents: cationic amphiphiles including local anesthetics such as bupivacaine, cationic lipids, liposomes or lipidic particles; polycations such as polylysine; branched, three-dimensional polycations such as dendrimers; carbohydrates; detergents; or surfactants, including benzylammonium surfactants such as benzalkonium chloride. Non-exclusive examples of such facilitating agents or co-agents useful in this invention are described in U.S. Pat. Nos. 5,593,972; 5,703,055; 5,739,118; 5,837,533; 5,962,482; 6,127,170; 6,379,965; and 6,482,804; and International Patent Application No. WO03/093449, published 13 Nov. 2003 (multifunctional molecular complexes and oil/water cationic amphiphile emulsions), and WO99/21591, published 6 May 1999 ("Compositions and Methods for Delivery of Genetic Material"); the teaching of which is hereby incorporated by reference. U.S. Pat. Nos. 5,824,538; 5,643,771; and 5,877,159 teach delivery of a composition other than a polynucleotide composition, e.g., a transfected donor cell or a bacterium containing the dsRNA-encoding compositions of the invention.

In some embodiments, the dsRNA effector molecule or dsRNA expression vector is complexed with one or more cationic lipids or cationic amphiphiles, such as the compositions disclosed in U.S. Pat. No. 4,897,355 (Eppstein et al., filed Oct. 29, 1987); U.S. Pat. No. 5,264,618 (Felgner at al., filed Apr. 16, 1991); or U.S. Pat. No. 5,459,127 (Felgner of al., filed Sep. 16, 1993). In other embodiments, the dsRNA or dsRNA expression vector is complexed with a liposome/liposomic composition that includes a cationic lipid and optionally includes another component such as a neutral lipid (see, for example, U.S. Pat. No. 5,279,833 (Rose); U.S. Pat. No. 5,283,185 (Epand); and U.S. Pat. No. 5,932,241).

In other embodiments, the dsRNA effector molecules or dsRNA expression construct(s) are complexed with the multifunctional molecular complexes of U.S. Pat. Nos. 5,837,533; 6,127,170; and 6,379,965 (Boutin), or, desirably, the multifunctional molecular complexes or oil/water cationic amphiphile emulsions of WO03/093449, published 13 Nov. 2003, Satishchandran, the teaching of which is incorporated herein by reference. The latter application teaches a composition that includes a nucleic acid, an endosomolytic spermine that includes a cholesterol or fatty acid, and a targeting spermine that includes a ligand for a cell surface molecule. The ratio of positive to negative charge of the composition is between 0.1 to 2.0, preferably 0.5 and 1.5, inclusive; the endosomolytic spermine constitutes at least 20% of the spermine-containing molecules in the composition; and the targeting spermine constitutes at least 10% of the spermine-containing molecules in the composition. Desirably, the ratio of positive to negative charge is between 0.8 and 1.2, inclusive, such as between 0.8 and 0.9, inclusive. The targeting spermine is designed to localize the composition to a particular cell or tissue of interest. The endosomolytic spermine disrupts the endosomal vesicle and encapsulates the composition during endocytosis, facilitating release of the nucleic acid from the endosomal vesicle and into the cytoplasm or nucleus of the cell. Use of such a mixture of targeting spermine/endosomolytic spermine achieves not only transfection, but enhances expression as well.

A dsRNA effector molecule or a DNA expression vector encoding a dsRNA effector molecule of the invention may be complexed as taught in WO03/093449, with a mixture of 35% mannosyl spermine to 65% cholesteryl spermine to achieve targeted transfection of immune cells, e.g., macrophages, via the mannose receptor, when administered IV in mice. Targeted transfection of hepatocytes in vivo for delivery of dsR- NAs against hepatic viruses such as HCV may be accomplished through IV injection with a composition comprising a DNA or RNA expression vector as described herein complexed with a mixture (e.g., a 35%/65% ratio) of a lactosyl spermine (mono or trilactosylated) and cholesteryl spermine (containing spermine to DNA at a charge ratio of 0.8). Such compositions are especially useful for pharmaceutical applications and may readily be formulated in a suitable sterile, non-pyrogenic vehicle, e.g., buffered saline for injection, for parenteral administration, e.g., IV (including IV infusion), IM, SC, and for intraperitoneal administration, as well as for aerosolized formulations for pulmonary delivery via inhalation. In certain formulations, a DNA expression construct of the invention may be complexed with an endosomolytic spermine such cholesteryl spermine alone, without a targeting spermine; some routes of administration, such as intraperitoneal injection or infusion, may achieve effective hepatic delivery and transfection of a DNA construct and expression of a dsRNA effector molecules, e.g., multiple dsRNA hairpins effective against HCV. A DNA expression vector encoding a dsRNA effector molecule of the invention may also be formulated as a microemulsion for in vivo oral or parenteral, e.g., intravenous delivery, as taught in WO03/093449, the teaching of which is hereby incorporated by reference. Formulations desirably contain amphiphiles such as the local anaesthetic bupivacaine, cholesteryl spermine, benzalkonium chloride, or octyl spermine. In vivo experiments in mice suggest that oral administration results in significant delivery to the liver. Intravenous administration of microemulsions results in transfection of organs with large capillary beds, e.g., lung, liver, spleen, and kidney.

Transformation/transfection of the cell for research and other non-therapeutic purposes may occur through a variety of means including, but not limited to, lipofection, DEAE-dextran-mediated transfection, microinjection, calcium phosphate precipitation, viral or retroviral delivery, electroporation, or biolistic transformation. The RNA or RNA expression vector (DNA) may be naked RNA or DNA or local anesthetic complexed RNA or DNA (See U.S. Pat. Nos. 6,217,900 and 6,383,512, "Vesicular Complexes and Methods of Making and Using the Same", Pachuk et al.). Another desirable delivery technology for the dsRNAs or dsRNA expression constructs of the invention for pharmaceutical applications is the self-assembling Cyclosert™ two-component nucleic acid delivery system, based on cyclodextrin-containing polycations, which are available from Insert Therapeutics, Pasadena, Calif. (See Popielarski at al., Bioconjug. Chem. 14:672-8 (2003); Reineke & Davis, Bioconjug. Chem. 14:247-54 (2003); Reineke & Davis, Bioconjug. Chem. 14:255-61 (2003)). The first component is a linear, cyclodextrin-containing polycationic polymer that when mixed with DNA binds to the phosphate "backbone" of the nucleic acid, condensing the DNA and self assembling into uniform, colloidal nanoparticles that protect the DNA from nuclease degradation in serum. A second component is a surface modifying agent with a terminal adamantine-PEG molecule that when combined with the cyclodextrin polymer forms an inclusion complex with surface cyclodextrins and prevents aggregation, enhances stability and enables systemic administration. In addition, targeting ligands to cell surface receptors may be attached to the modifier providing for targeted delivery of DNA directly to target cells of interest. Since hepatocytes are susceptible to HCV infection, utilizing this method to target delivery of the dsRNA expression constructs of the invention to liver cells is considered especially advantageous. E.g., the asialoglycoprotein receptor (ASGP-R) on mammalian hepatocytes may be targeted by use of synthetic ligands with galactosylated or lactosylated residues, such as galactosylated polymers. Appropriate regulatory sequences can be inserted into the vectors of the invention using methods known to those skilled in the art, for example, by homologous recombination (Graham at, J. Gen. Virol. 36:59-72 (1977)), or other appropriate methods (Molecular Cloning: A Laboratory Manual, Sambrook et al., eds., Cold Spring Harbor Laboratory, 2nd Edition, Cold Spring Harbor, N.Y., 1989).

Promoters are inserted into the vectors so that they are operably linked 5' to the nucleic acid sequence encoding the dsRNA oligonucleotide. Any promoter that is capable of directing initiation of transcription in a eukaryotic cell may be used in the invention. For example, non-tissue-specific promoters, such as the cytomegalovirus (DeBernardi at al., Proc. Natl. Mad. Sci. USA 88:9257-9261 (1991) and references therein), mouse metallothionine I gene (Hammer at, J. Mol. Appl. Gen. 1:273-288 (1982)), HSV thymidine kinase (McKnight, Cell 31:355-365 (1982)), and SV40 early (Benoist at, Nature 290:304-310 (1981)) promoters may be used. Viral promoters and enhancers, such as those from cytomegalovirus, herpes simplex viruses (types I and II), hepatitis viruses (A, B, and C), and Rous sarcoma virus (RSV; Fang at al., Hepatology 10:781-787 (1989)), may also be used in the invention. dsRNA expression vectors may include promoters for RNA polymerase I, RNA polymerase II including but not limited to HCMV, SCMV, MCMV, RSV, EF2a, TK and other HSV promoters such as ICP6, ICP4 and ICP0 promoters, HBV pregenomic promoter, RNA pol III promoter including but not limited to U6 and tRNA promoters, mitochondrial light and heavy strand promoters. Desirably, the dsRNA expression vector comprises at least one RNA polymerase II promoter, for example, a human CMV-immediate early promoter (HCMV-IE) or a simian CMV (SCMV) promoter, at least one RNA polymerase I promoter, or at least one RNA polymerase III promoter. The promoter may also be a T7 promoter, in which case, the cell further comprises T7 RNA polymerase. Alternatively, the promoter may be an SP6 promoter, in which case, the cell further comprises SP6 RNA polymerase. The promoter may also be one convergent T7 promoter and one convergent SP6 RNA promoter. A cell may be made to contain T7 or SP6 polymerase by transforming the cell with a T7 polymerase or an SP6 polymerase expression plasmid, respectively. In some embodiments, a T7 promoter or a RNA polymerase III promoter is operably linked to a nucleic acid that encodes a short dsRNA. In other embodiments, the promoter is a mitochondrial promoter that allows cytoplasmic transcription of the nucleic acid in the vector (see, for example, the mitochondrial promoters described in WO 00/63364, filed Apr. 19, 2000, and in WO/US2002/00543, filed 9 Jan. 2001). Alternatively, the promoter is an inducible promoter, such as a lac (Cronin et al., Genes Dev. 15:1506-1517 (2001)), are (Khiebnikov et al., J. Bacteriol. 182:7029-34 (2000)), ecdysone (Rheogene website), RU48 (mefepristone) (corticosteroid antagonist) (Wang at al., Proc. Natl. Acad. Sci. USA 96:8483-88 (1999)), or tet promoter (Rendal at al., Hum. Gene Ther. 13:335-42 (2002); Lamartina et al., Hum. Gene Ther. 13:199-210 (2002)) or a promoter disclosed in WO 00/63364, filed Apr. 19, 2000. Also useful in the methods and compositions of the invention are the structural and chimeric promoters, including the forced open padlock promoters, taught in WO 03/035910 A1, re-published 23 Dec. 2004. See also the promoter systems taught in Pachuk, C., and Satishchandran, C., "Multiple-Compartment Eukaryotic Expression Systems," U.S. Provisional Application No.

60/497,304, filed 22 Aug. 2003, which are considered particularly desirable in the methods and compositions of the invention.

A desirable method of the invention utilizes a T7 dsRNA expression system to achieve cytoplasmic expression of dsRNA, (e.g., long or short dsRNA molecules) in vertebrate cells (e.g., mammalian cells). The T7 expression system utilizes the T7 promoter to express the desired dsRNA. Transcription is driven by the T7 RNA polymerase, which can be provided on a second plasmid or on the same plasmid. Bacteriophage T7 RNA polymerase (T7 Pol) is the product of T7 gene 1, which can recognize its responsive promoter sequence specifically and exhibit a high transcriptase activity. The complete sequence of the T7 genome, with detailed information about the different regions of the bacteriophage, including promoter sequences, is disclosed in Dunn & Studier, J. Mol. Biol. 166:477-535 (1983) (see also NCBI 'Genome' database, Accession No. NC 00 1 604). The T7 promoter cannot be utilized by any RNA polymerase other than the polymerase of bacteriophage T7, which shows a stringent specificity for the promoter (Chamberlin of al., Nature 228:227-31 (1970)). When utilizing the T7 expression system for expressing dsRNAs, for example, a first plasmid construct that expresses both a sense and antisense strand under the control of converging T7 promoters and a second plasmid construct that expresses the T7 RNA polymerase under the control of an RSV (Rous Sarcoma Virus) or CMV promoter can be used. Both the dsRNA and the T7 RNA polymerase could advantageously be expressed from a single bicistronic plasmid construct, particularly when the dsRNA is formed from a single RNA strand with inverted repeats or regions of self-complementarity that enable the strand to assume a stem-loop or hairpin structure with an at least partially double-stranded region. Individual sense and antisense strands which self assemble to form a dsRNA can be synthesized by a single plasmid construct using, e.g., converging promoters such as bacteriophage T7 promoters placed respectively at the 5' and 3' ends of the complementary strands of a selected sequence to be transcribed. See also, e.g., the teaching of WO 0063364, with respect to T7 dsRNA expression systems, as well as U.S. Ser. No. 60/399,998, filed 31 Jul. 2002, and U.S. Ser. No. 60/419,532, filed 18 Oct. 2002.

The dsRNAs of the invention, and the recombinant vectors containing nucleic acid sequences encoding them, may be used in therapeutic compositions for preventing infection by single-stranded viruses. The therapeutic compositions of the invention may be used alone or in admixture, or in chemical combination, with one or more materials, including other antiviral agents. Combination therapy of the agents of the invention and other antivirals is expected to significantly increase the efficacy of therapy while substantially reducing the development of drug resistance. Specific dosage regimens involving therapy with such multiple agents can be determined through routine experimentation by those of ordinary skill in the art of clinical medicine.

Formulations will desirably include materials that increase the biological stability of the oligonucleotides or the recombinant vectors, or materials that increase the ability of the therapeutic compositions to penetrate infected cells selectively. The therapeutic compositions of the invention may be administered in pharmaceutically acceptable carriers (e.g., physiological saline), which are selected on the basis of the mode and route of administration, and standard pharmaceutical practice. One having ordinary skill in the art can readily formulate a pharmaceutical composition that comprises an oligonucleotide or a gene construct. In some cases, an isotonic formulation is used. Generally, additives for isotonicity can include sodium chloride, dextrose, mannitol, sorbitol, and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free. Suitable pharmaceutical carriers, as well as pharmaceutical necessities for use in pharmaceutical formulations, are described in *Remington: The Science and Practice of Pharmacy* (formerly *Remington's Pharmaceutical Sciences*), Mack Publishing Co., a standard reference text in this field, and in the USP/NF.

Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intravenous, intramuscular, oral, intraperitoneal, intradermal, intraarterial and subcutaneous injection. dsRNAs or dsRNA expression constructs may be administered by means including, but not limited to, traditional syringes, needleless injection devices, or "microprojectile bombardment gene guns". Alternatively, the dsRNA and/or dsRNA expression construct may be introduced by various means into cells that are removed from the individual. Such means include, for example, ex vivo transfection, electroporation, microinjection and microprojectile bombardment. After the gene construct is taken up by the cells, they are reimplanted into the individual. It is contemplated that otherwise non-immunogenic cells that have gene constructs incorporated therein can be implanted into the individual even if the host cells were originally taken from another individual.

For administration of a dsRNA effector molecule of the invention (e.g., a short or long dsRNA to silence a gene) to an animal, typically between 10 mg to 100 mg, 1 mg to 10 mg, 500 µg to 1 mg, or 5 µg to 500 µg dsRNA is administered to a 90-150 pound person/animal (in order of increasing preference). For administration of a vector encoding a dsRNA (e.g., a short or long dsRNA to silence a gene) to an animal, typically between 100 mg to 300 mg, 10 mg to 100 mg, 1 mg to 10 mg, 500 µg to 1 mg, or 50 µg to 500 µg dsRNA expression vector or construct is administered to a 90-150 pound person/animal (in order of increasing preference). The dose may be adjusted based on the weight of the animal. In some embodiments, about 1 to 10 mg/kg or about 2 to 2.5 mg/kg is administered. Other doses may also be used, as determined through routine experimentation by those of skill in the art of clinical medicine.

For administration in an intact animal, typically between 10 ng and 50 µg, between 50 ng and 100 ng, or between 100 ng and 5 µg of dsRNA or DNA encoding a dsRNA is used. In desirable embodiments, approximately 10 µg of a DNA or 5 µg of dsRNA is administered to the animal. With respect to the methods of the invention, it is not intended that the administration of dsRNA or DNA encoding dsRNA to cells or animals be limited to a particular mode of administration, dosage, or frequency of dosing; the present invention contemplates all modes of administration sufficient to provide a dose adequate to inhibit a viral infection, prevent a viral infection, or treat a viral infection.

If desired, short dsRNA is delivered before, during, or after the exogenous delivery of dsRNA (e.g., a longer dsRNA) that might otherwise be expected to induce cytotoxicity. See the teaching of U.S. Ser. No. 10/425,006, filed 28 Apr. 2003, "Methods of Silencing Genes Without Inducing Toxicity", Pachuk.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples, while indicating preferred embodiments of the invention, are given by way of illustration only. For example, siRNA sequences used herein as the Effector Sequence or Effector Complement of dsRNA molecules, comprise 21 nucleotides identical to the target sequences, however it is intended that the dsRNA effector molecules of the invention may be dsRNA duplexes (comprising Effector Sequences and Effector Complements) of various lengths, e.g., 19, 20, 21, 22, 23, 24, 25, 26, 27, 28, or longer, e.g., 50, 100 or more basepairs, particularly where the dsRNA molecules are expressed intracellularly, in which case dsRNA stress responses are not evoked, even by longer dsRNAs. Similarly, a "hairpin dsRNA", a "dsRNA hairpin", "short-hairpin RNA" or "shRNA", may be utilized, i.e., an RNA molecule of less than approximately 400 to 500 nucleotides (nt), preferably less than 100 to 200 nt, in which at least one stretch of at least 15 to 100 nucleotides (preferably 17 to 50 nt, more preferably 19 to 29 nt) is based paired with a complementary sequence located on the same RNA molecule (single RNA strand), and where said sequence ("Effector Sequence") and complementary sequence ("Effector Complement") are separated by an unpaired region of at least about 4 to 7 nucleotides (preferably about 9 to about 15 nucleotides) which forms a single-stranded loop above the stem structure created by the two regions of base complementarity. These various embodiments are within the scope of this invention. From the above discussion and these Examples, one skilled in the art can ascertain the preferred features of this invention, and without departing from the spirit and scope thereof, can make various changes and modifications of the invention to adapt it to various uses and conditions.

Experimental details and results are shown below. These experiments compare results obtained with siRNAs designed to target the plus strand of HCV vs. results obtained with siRNAs designed to target the minus strand of HCV. The method used to design siRNAs for the plus strand and the minus strand is described after the confirmatory experimental data.

Example 1

Plus Strand Targeting

Brief Introduction:
The hepatitis C virus (HCV) is the primary cause of non-A, non-B transfusion-associated hepatitis and accounts for more than 200 million hepatitis cases worldwide. The HCV genome has a high degree of sequence variability. There are six major genotypes comprising more than fifty subtypes and significant heterogeneity hallmarked by quasi-species has been found within patients. Great progress in understanding HCV replication has been made by using recombinant polymerases or cell-based subgenomic replicon systems. By using the replicon cell system, siRNA has been demonstrated to be able to suppress HCV protein expression and RNA replication. Sequences of the 5' NTR and both structural and nonstructural genes have been targeted successfully. U.S. Pat. No. 5,874,565, "Nucleic Acids Comprising a Highly Conserved Novel 3' Terminal Sequence Element of the Hepatitis C Virus", teaches a highly conserved 101 nt sequence believed to be important in HCV replication, which makes it a potentially attractive target for dsRNA-mediated silencing. However, the feasibility of using the 3' NTR as an effective anti-viral target for RNAi has not been established, much less the feasibility of preferentially targeting the minus strand replication intermediate of this plus strand sequence with specially designed dsRNA effector molecules. This sequence and other conserved sequences of HCV, including 5' UTR sequences, as taught in "Conserved HBV and HCV Sequences Useful for Gene Silencing", WO2005/014806, published 17 Feb. 2005, and in U.S. Provisional Application No. 60/638,294, filed 22 Dec. 2004, provide a pool of conserved sequences to be used for targeting the HCV minus strand replication intermediate (anti-genomic RNA) of the plus strand HCV, and optionally, the plus strand genomic RNA as well.

"Targeting" as used herein in the context of dsRNA effector molecules means increasing the likelihood that an RNA molecule ("the Effector Strand") of opposite polarity and complementary to a selected viral strand will associate with the RISC. "Targeting" may be a matter of selecting sequences from this pool according to the principles provided herein. For example, since the terminus of a dsRNA effector molecule with the lower thermal stability will have a greater propensity to separate into its composite strands, a particular conserved region of between 19 and 27 basepairs, e.g., 19, 20, 21, 22, 23, 24, 25, 26, or 27, may be selected to target a particular viral strand. That is, the strand whose 5' end is present in a duplex having a lower thermal stability relative to its 3' end will be more likely than its complement strand to be incorporated into the RISC. A known conserved viral sequence may be chosen to meet this criterion, as taught herein. In other embodiments of the invention, targeting may involve introducing one or possibly two nucleotide mismatches within the three to five terminal nucleotides of the Effector Complement strand of the dsRNA effector molecule, as just one of several methods used to permit the thermal stability of one terminus of the dsRNA effector molecule to be lowered so that a conserved sequence may is modified to target an opposite strand replication intermediate as taught herein.

Figure 3:
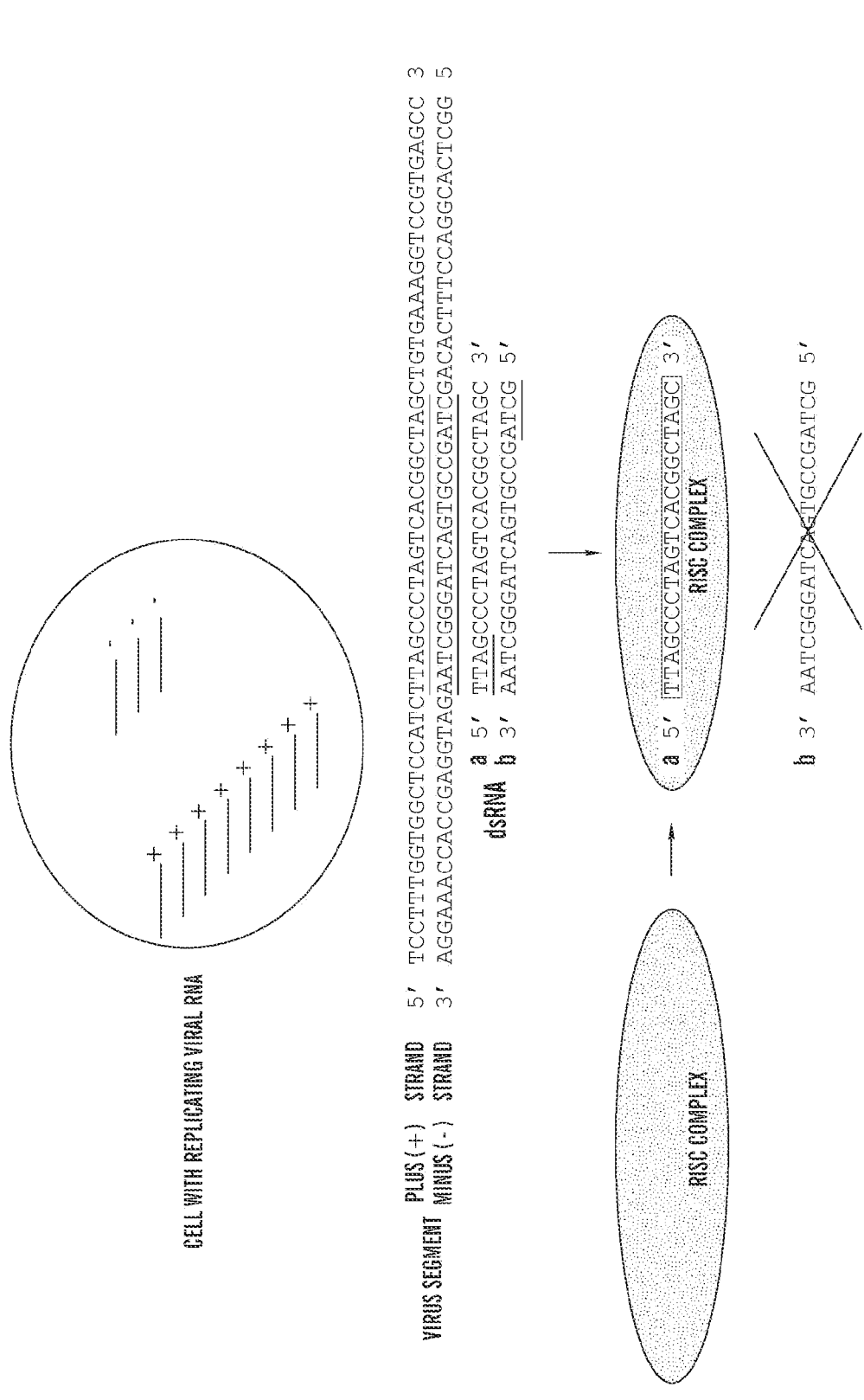
FIG. 3 is a diagram of strand-specific targeting by dsRNA. A schematic view is presented of a cell infected with a plus-stranded RNA virus, such as hepatitis C virus (HCV). The virus produces minus strand copies of its genome during the process of replication, but these are present in significantly lower quantities than the plus strand. The sequence of a short segment of HCV (starting at nucleotide 9502 in Genbank Accession No. AJ238799) is shown in detail in the center of the diagram. Both the genomic (plus) strand of the virus and the replication intermediate (minus) strand of the virus are represented, aligned to indicate their base complementarity. A 21 bp region was selected (underlined) for design of the indicated dsRNA molecule. Both the "effector" strand (boxed, labeled "a") and its complement, labeled "b" are shown. Only the "a" strand will be incorporated into the dsRNA silencing complex (RISC) because it's 5' end is less thermodynamically stable than the 5' end of the "b" strand, due to the greater proportion of A and T residues in the terminal 5 bases. Since only the "a" strand is favored for RISC complex incorporation and since it is complementary only to the viral minus strand RNA, this dsRNA molecule will target the viral minus strand, not the plus strand for degradation. The figure discloses SEQ ID NOS: 60-61, 12, 62, 12 & 62, respectively, in order of appearance.

Here we report the design and testing of several siRNAs that can inhibit HCV protein expression in the subgenomic replicon system. Although synthetically prepared siRNAs were used for convenience, it will be recognized by those of skill in the art of molecular biology that the results achieved are equally applicable to expressed dsRNA effector molecules, including shRNA effector molecules, as well as methods of making and using them, as taught herein.

siRNA Design:
Each 21 bp sequence from the HCV 3' NTR selected for dsRNA targeting was used to design a pair of DNA oligonucleotides representing both complementary strands of the sequence, plus an additional 9 bp tail corresponding to the T7 RNA polymerase promoter. The process of strand-specific targeting was accomplished by starting from the sequence of either the minus or plus strand as desired, and choosing an Effector Strand sequence (complementary to the target) with a 5' end present in a duplex of lower thermodynamic stability than the 3' end, in a simplification of rules described by Reynolds et al., Nature Biotechnol. 22:326-30 (2004); Schwartz et al., Cell 115:199-208 (2003); and Khvorava et al., Cell 11 5:209-16 (2003). (See FIG. 3). Each tailed oligonucleotide was then used as template in in vitro transcription reactions which generated large amounts of single-stranded RNA complementary to the template sequence in each reaction (in vitro transcription was performed using a kit manufactured by Ambion). After purification, the complementary RNA products were annealed to form dsRNA, which was used in transfection. For purposes of this experiment, the target sequence was the 101 nt 3' UTR as taught in Rice, U.S. Pat. No. 5,874,565.

Other conserved HCV sequences suitable for selection and utilization in siRNAs and shRNAs according to the principles of the invention are taught in "Conserved HBV and HCV Sequences Useful for Gene Silencing", WO2005/014806, published 17 Feb. 2005, and in U.S. Provisional Application No. 60/638,294, filed 22 Dec. 2004, in particular the conserved HCV sequences disclosed therein, i.e., SEQ ID NO:11, SEQ ID NO:12, and SEQ ID NO:27 and HCV Conserved Region 1 and HCV Conserved Region 2, incorporated herein by reference.

Cell Culture and Media.

The HCV replicon hepatoma cell line Huh 7 9-13 (Ralf Bartenschlager) was cultured in Dulbecco's Modified Eagle Media (DMEM) (Invitrogen) containing 10% fetal calf serum (Invitrogen), 1% penicillin-streptomycin, 1% non-essential amino acids, and 0.5 mg/ml Geneticin® (Invitrogen). Cells were grown to 75% confluency prior to splitting.

Western Blot Analysis.

Total cell lysates from replicon cells were harvested in 1×LDS Buffer (Invitrogen). The lysates were heated at 90° C. for 5 min. in the presence of beta-mercaptoethanol before electrophoresis on a 10% Tris-Glycine polyacrylamide gel (Invitrogen). The protein was transferred to polyvinylidene difluoride (PVDF) membrane (Invitrogen). Following the transfer, the membrane was rinsed once with PBS containing 0.5% Tween-20 (PBS-Tween) and blocked in PBS-Tween containing 5% non-fat milk for 1 hr. After washing with PBS-Tween, the membrane was incubated with primary α-NS5A antibody (a gift from Dr. Chen Liu) at 1:1500 dilution for 1 hr. at room temperature. Prior to incubation with horse radish peroxidase (HRP) conjugated α-mouse IgG secondary antibody (Amersham) diluted 1:5000, the blot was washed in PBS-Tween 20. Following the secondary antibody incubation, the blot was washed again and treated with ECL (electrochemiluminesence) (Amersham) according to the manufacturer's protocol.

Transfection of siRNA into Replicon Cells.

For transfection of siRNA into replicon cells, the Lipofectamine® 2000 reagent (Invitrogen) was used according to the user manual. Briefly, $2\times10^4$ cells in 0.5 ml of DMEM were seeded in 24 well plates one day before the transfection. The indicated amount of siRNA was diluted in 50 μl OptiMEM® and mixed with diluted Lipofectamine® 2000 reagent (1 μl in 50 μl of OptiMEM®). The mixture was incubated at room temperature for 20 min. before applied onto the cell monolayer. 48-72 hours after transfection, cells were washed in PBS and lysed in 100 μl SDS sample buffer.

FIG. 1 is a Western Blot showing levels of HCV NS5A protein at (left to right) 0, 9, and 20 pmole of the identified siRNAs, delivered as described in the text Lamin siRNA serves as a negative control and core siRNA serves as a positive control. There is no inhibition of NS5A when any concentration of a lamin siRNA is used while inhibition is seen at both 9 and 20 pmole with the positive control siRNA. Significant down regulation is only seen with siRNA 72 (SEQ ID NO:7). Table 1 lists the sequences of the siRNAs designed to target the plus strand of the 3' NTR. Sequences are expressed as the plus strand (5'→3'). Sequence Reference refers to the corresponding region of HCV strain 1b (GenBank accession no. AJ238799).

TABLE 1

| Sequence Reference | FIG. 1 Reference | SEQ ID NO | Sequence |
|---|---|---|---|
| 9382-9402 | 12 | SEQ ID NO: 1 | GCTAAACACTCCAGGCCAATA |
| 9502-9522 | 22 | SEQ ID NO: 2 | TCCTTTGGTGGCTCCATCTTA |
| 9512-9532 | 32 | SEQ ID NO: 3 | GCTCCATCTTAGCCCTAGTCA |
| 9518-9538 | 42 | SEQ ID NO: 4 | TCTTAGCCCTAGTCACGGCTA |
| 9525-9545 | 52 | SEQ ID NO: 5 | CCTAGTCACGGCTAGCTGTGA |
| 9526-9546 | 62 | SEQ ID NO: 6 | CTAGTCACGGCTAGCTGTGAA |
| 9552-9572 | 72 | SEQ ID NO: 7 | CGTGAGCCGCTTGACTGCAGA |
| 9577-9597 | 82 | SEQ ID NO: 8 | GCTGATACTGGCCTCTCTGCA |
| 9579-9599 | 92 | SEQ ID NO: 9 | TGATACTGGCCTCTCTGCAGA |
| 9583-9603 | 102 | SEQ ID NO: 10 | ACTGGCCTCTCTGCAGATCAA |

Example 2

Minus Strand Targeting

Example 2 was performed as described in Example 1 except that siRNAs R1-R8 were used in transfections. The Western Blot assay performed here was as described in Example 1. The control HCV core siRNA used as a positive control is the siRNA described in the previous HCV Example 1. All siRNAs evaluated map to the 3' UTR of the HCV genome and are conserved amongst HCV genotypes and quasi-species.

FIG. 2 is a Western Blot showing levels of HCV NS5A protein at (left to right) 0, 9, and 20 pmole of the identified siRNA, and 0, 3, and 9 pmole of the core positive control siRNA. siRNAs R1 (SEQ ID NO:23), R2 (SEQ ID NO:22), R3 (SEQ ID NO:21), R5 (SEQ ID NO:19), and R7 (SEQ ID NO:17) all exhibited significant inhibition of HCV. Additionally, siRNA of SEQ ID NO:11, SEQ ID NO:12, SEQ ID NO:13, SEQ ID NO:14, and SEQ ID NO:15 also were effective at specifically targeting the minus strand (data not shown). Table 2 lists the sequences of the siRNAs used in Example 2. Sequences are expressed as the plus strand (5'→3'). Sequence Reference refers to the corresponding region of HCV strain 1b (GenBank accession no. AJ238799).

TABLE 2

Figure 2:
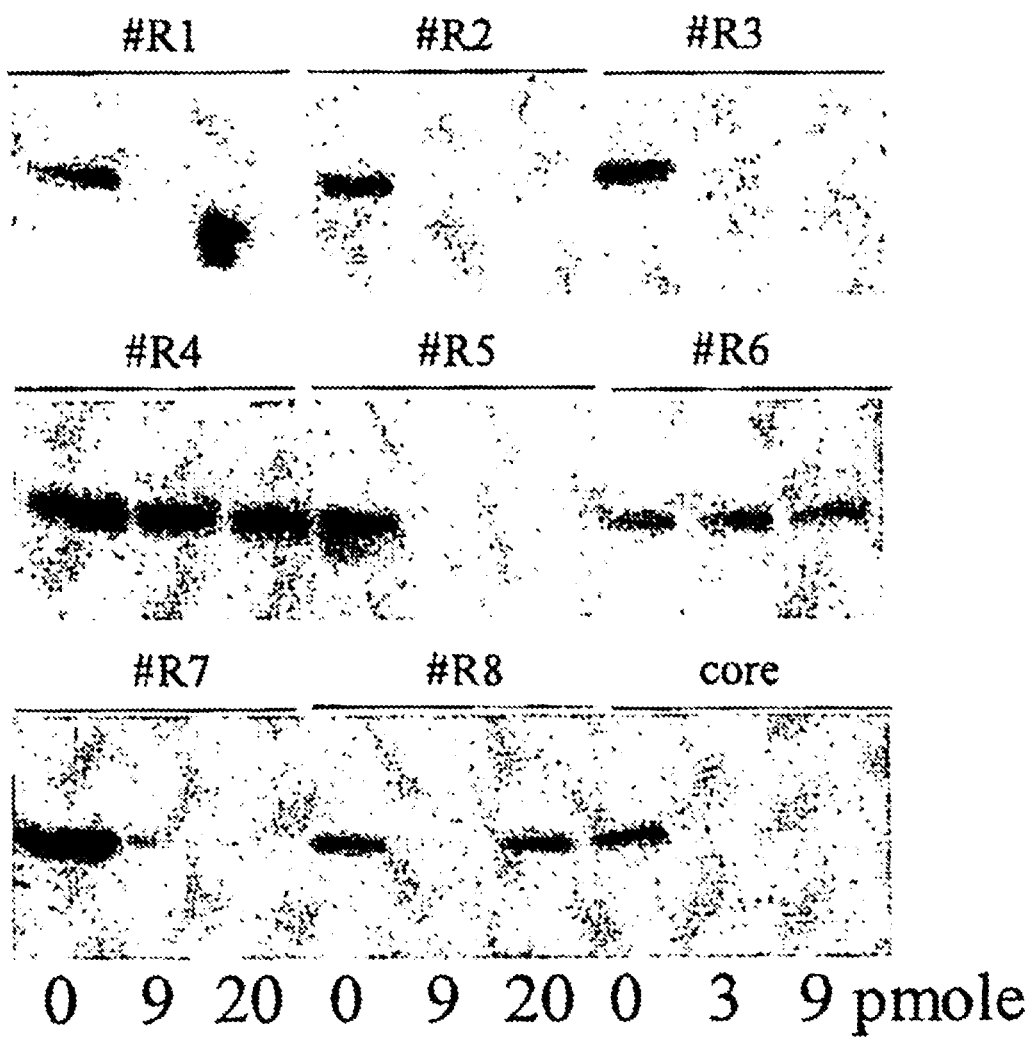
FIG. 2 is a Western Blot showing levels of HCV NS5A protein at (left to right) 0, 9, and 20 pmole of the identified siRNA, and 0, 3, and 9 pmole of the core positive control siRNA.

| Sequence Reference | FIG. 2 Reference | SEQ ID NO | Sequence |
|---|---|---|---|
| 9509-9529 | — | SEQ ID NO: 11 | GTGGCTCCATCTTAGCCCTAG |
| 9520-9540 | — | SEQ ID NO: 12 | TTAGCCCTAGTCACGGCTAGC |
| 9534-9554 | — | SEQ ID NO: 13 | GGCTAGCTGTGAAAGGTCCGT |
| 9560-9580 | — | SEQ ID NO: 14 | GCTTGACTGCAGAGAGTGCTG |
| 9581-9601 | — | SEQ ID NO: 15 | ATACTGGCCTCTCTGCAGATC |
| 9506-9526 | R8 | SEQ ID NO: 16 | TTGGTGGCTCCATCTTAGCCC |
| 9514-9534 | R7 | SEQ ID NO: 17 | TCCATCTTAGCCCTAGTCACG |
| 9520-9540 | R6 | SEQ ID NO: 18 | TTAGCCCTAGTCACGGCTAGC |
| 9537-9557 | R5 | SEQ ID NO: 19 | TAGCTGTGAAAGGTCCGTGAG |
| 9544-9563 | R4 | SEQ ID NO: 20 | GAAAGGTCCGTGAGCCGCTT |
| 9554-9574 | R3 | SEQ ID NO: 21 | TGAGCCGCTTGACTGCAGAGA |
| 9567-9587 | R2 | SEQ ID NO: 22 | TGCAGAGAGTGCTGATACTGG |
| 9584-9604 | R1 | SEQ ID NO: 23 | CTGGCCTCTCTGCAGATCAAG |

Conclusions:

The results described above in Examples 1 and 2 indicate that the plus or minus RNA strands of a plus strand RNA virus can be purposefully targeted by designing the effector siRNAs appropriately. In the Examples presented here, targeting of the minus strand was, in general, a more effective method of down-regulating viral protein expression. Furthermore, dsRNAs designed to target the negative strand are more likely to be active. Out of a total of 12 siRNAs targeted to the minus strand, 10 of the siRNAs demonstrated a reduction in viral protein expression, while out of 13 siRNAs targeted to the plus strand (of which the results of 9 are shown in FIG. 1), only 2 siRNAs were effective in reducing protein expression. This result demonstrates that this siRNA design approach, which considers the viral replicative intermediate RNA (minus strand) as a viable substrate for RNAi distinct from its more abundant plus strand counterpart has superior advantages in the selection of potent antiviral agents.

Example 3

DNA Plasmid Vector Expressing 4 shRNAs Targeting the Negative Strand of HCV

In this example, the siRNA sequences given as R1, R2, R5, and R7 in FIG. 2 are generated intracellularly by expression from a plasmid vector transfected into the cell; the vector is made by cloning oligonucleotides encoding the four short hairpin (shRNA) forms of the siRNAs each under the control of a different RNA polymerase III promoter in a single vector (i.e., four RNA polymerase III promoters each operably linked to a sequence encoding one of the four shRNAs). In these shRNA trancripts, the Effector Strand is joined to the Effector Complement strand via a 9 base "loop" sequence (AGAGAACUU).

Using standard recombinant DNA techniques, a plasmid containing a bacterial antibiotic selection marker and origin of replication is selected as the starting point for the insertion of the specific promoter/shRNA combinations below. The plasmid is made by first combining an approximately 1 kb fragment (containing the bacterial origin of replication, between the ampicillin resistance gene and the multiple cloning site) of the widely available pUC18 vector (Yanisch-Perron et al, Gene, 114:81 (1985)) with a chimeric kanamycin resistance gene as disclosed in U.S. Pat. No. 5,851,804. A variety of commercially-available plasmid vectors obtainable from suppliers such as Invitrogen, Clontech, Stratagene and others may be used as an alternative source of vector elements, or to substitute for Applicants' vector for use as starting material to produce functionally equivalent variants of the vectors described below. The methods used to assemble the vector from source sequences include restriction enzyme digestion, gel electrophoresis, PCR (polymerase chain reaction), DNA sequencing, enzymatic ligation, and "chain reaction cloning", as described in U.S. Pat. No. 6,143,527, "Chain reaction cloning using a bridging oligonucleotide and DNA ligase", Pachuk et al., and other methods common and well known to those skilled in the art.

It is expedient to prepare single Pol III promoter vector constructs prior to generating the multiple promoter constructs. A basic single-promoter RNA pol III vector for expressing single short hairpin RNAs (shRNA) is generated by enzymatic joining of the origin-of-replication restriction fragment above (on) to the chimeric kanamycin resistance gene, and then to a desired Pol III promoter/shRNA expression cassette in sequential steps. The promoter/shRNA expression cassettes are made by joining the promoter with short fragments (approximately 50 to 60 bp) comprising the shRNA sequence of interest, made as synthetic, double-stranded, oligonucleotides by custom order from a commercial vendor. The purpose of constructing single-promoter vectors as precursors to multiple promoter vectors embodies several beneficial aspects: First, it allows for the functional confirmation of each promoter/shRNA pair in the absence of other Pol III expression elements or shRNAs which could confound the means of detection of the object promoter/shRNA pair or elements. Second, it allows for DNA sequencing of all or part of each cassette using sequencing primers which otherwise would have multiple annealing sites in multiple promoter vectors, and render sequencing in that context impossible. Third, the verified single-promoter cassettes can be efficiently mobilized for cloning into any number of incipient multiple-promoter vectors by the intentional design of cloning restriction site pairs which are unique for each promoter element.

Following the determination of adequate expression levels and gene silencing effects of the single-promoter vectors, multiple-promoter vectors are constructed from the single-promoter vector promoter/shRNA cassettes in a stepwise fashion to contain, 4 Pol III promoters each driving the expression of a different shRNA. Thus, an effective single-promoter construct expressing a shRNA is modified to add a second promoter-shRNA cassette. The positioning of the second cassette relative to the first cassette is chosen empirically by generating several alternative 2-promoter forms of the two-promoter plasmid (varied by the relative positions of the 1$^{st}$ and 2$^{nd}$ cassette with respect to the other vector elements, and varied by the orientation of each cassette with respect to direction of transcription). It will be appreciated by one skilled in the art that when attempting to combine 2 cassettes for optimal expression in a single vector, that the position around the circular vector as well as the "backward" or "forward" transcriptional directionality of the cassette can be varied to produce as many as 8 different varieties, all containing the same elements. Moreover, when attempting the expression of 2 different shRNA elements from two different promoters in this vector, the different combinations of shRNA sequence with each of the two promoters would produce 16 different variants of said vector, again all containing the same elements, but in different arrangements. Applicants have observed that these different configurations can result in a significant variation in the apparent levels of expression of each shRNA. Nevertheless, the multiple polymerase III promoter constructs as described here and in U.S. Provisional Applications 60/362,260 and 60/629,942, filed 23 Aug. 2004 and 22 Nov. 2004, respectively, and in PCT/2005/29976 filed 23 Aug. 2005, entitled "Multiple RNA Polymerase III Promoter Expression Constructs", will demonstrate that an efficient selection of relatively optimized configurations of these elements for the purpose of expressing the multiple effector RNAs (particularly shRNA) for gene silencing effects can be accomplished without undue experimentation.

RNA polymerase III type-3 (U6-type) promoters, including U6, H1, and 7SK, etc. (e.g., human, murine, bovine or other mammalian forms) are preferred for expression of dsRNA effector molecules of the invention. In this example, the U6 and 7SK promoter/shRNA cassettes are placed adjacent to each other in the multiple cloning site of the vector, while a distal cloning site (adjacent to the kanamycin resistance gene) is used for a third and fourth promoter sequence (either a second copy of the U6 promoter, the 7SK promoter or the H1 promoter). The 5' end of each shRNA element is joined to the 3' end of each promoter using a convenient restriction site, e.g., Sal I or HinduIII, engineered by introducing 6 nt between the 3' end of the promoter and the start of the shRNA sequence. Each promoter cassette contains a stretch of 5 thymidine residues at the 3' end to serve as a transcription terminator. Thus, the predicted transcript which includes the dsRNA hairpin actually contains additional 5' and 3' sequences: a 5' leader consisting of 6 bases (e.g., the Sal I or HindIII or other chosen recognition sequence), followed by the dsRNA hairpin sequences, followed by a short 3' terminal U tract, usually two (1, 2, 3, or 4) U residues incorporated during transcription termination. The choice of a Sal I or HindIII site is a matter of convenience, and it will be recognized that any number of other restriction sites, preferably 6 or 8 cutters could be utilized instead, in which case, the dsRNA hairpin transcript will include a different 5' leader sequence. The principle of cloning a DNA segment encoding an shRNA for expression by a single promoter is also well illustrated in cloning vectors and instruction manuals commercially available from Ambion, Inc. (Austin, Tex., USA).

The completed expression vectors are then produced in *E. coli* bacteria according to standard methods, and transfected into huh7 cells containing HCV replicons as in the previous examples. The vector can be demonstrated to express all 4 shRNAs targeting the negative strand of HCV and it can be shown using Northern blotting, PCR or nuclease protection analysis of cellular RNA that the negative strand of the virus is reduced by 20% or more, relative to cells transfected with a control vector which contains highly mutated permutations of the shRNA sequences.

Example 4

A DNA plasmid vector expressing multiple shRNAs, including shRNAs targeting conserved sequences of both the negative strand (anti-genomic strand) and the positive strand (genomic strand) of the 3' UTR of HCV.

In this example, the methods and procedures of Example 3 are followed with the exception that only two of the shRNA sequences targeting the negative strand (e.g., any two selected from SEQ ID NO: 23 or 22 or 19 or 17 from Table 2) are included in the expression vector (for example R1 and R2, or R5 and R7, etc) and the other two expression cassettes are used for including shRNAs corresponding to plus-strand targeting sequitopes, (in this case both targeting a conserved sequence of the (+) strand of the HCV 3' UTR or "X" region), e.g., SEQ ID NO:7, and an shRNA based on siRNA number 122, (SEQ ID NO:59). The sequences encoding the selected shRNAs are cloned into the plasmid expression vector, each operably linked to a polymerase 111 promoter, which may be the same or different, e.g., U6, 7SK, H1, etc.

Example 5

DNA plasmid vector expressing multiple shRNAs, including shRNAs that target conserved sequences of both the 5' and 3' UTRs of both the negative (anti-genomic strand) and positive (genomic) strands of HCV.

In this example, the methods and procedures of Example 3 are followed with the exception that sequences encoding shRNAs targeting both the HCV (+) strand 3' UTR and the HCV (−) strand 3' UTR (e.g, SEQ ID NO:7 or SEQ ID NO:59, and a sequence selected from, e.g., SEQ ID NO: 23 or 22 or 19 or 17) are cloned into the expression vector, and in addition, conserved sequences encoding shRNAs targeting both the HCV (+) strand 5' UTR (e.g. SEQ. ID No: 24, 26, 28, 30, 32, 34, 38, 40, 42, 45, 47, or 49) and the HCV (−) strand 5' UTR (SEQ. ID NO: 25, 27, 29, 39, 41, 46, 48, 50, or 52) are selected and cloned into the expression vector, e.g., each operably linked to a polymerase III promoter, which may be the same or different, e.g., U6, 7SK, H1, etc.

The invention claimed is:

1. A method of inhibiting the replication of Hepatitis C Virus (HCV) in a vertebrate cell infected by said virus, the method comprising administering to said vertebrate cell
- a first double-stranded (ds) RNA effector molecule comprising an effector sequence consisting of SEQ ID NO: 17 and an effector complement of SEQ ID NO: 17,
- a second dsRNA effector molecule comprising an effector sequence consisting of SEQ ID NO: 19 and an effector complement of SEQ ID NO: 19,
- a third dsRNA effector molecule comprising an effector sequence consisting of SEQ ID NO: 22 and an effector complement of SEQ ID NO: 22, and
- a fourth dsRNA effector molecule comprising an effector sequence consisting of SEQ ID NO: 23 and an effector complement of SEQ ID NO: 23,
- wherein U is substituted for T.

2. The method of claim 1, wherein the vertebrate cell is a human cell.

3. The method of claim 1, wherein the dsRNA effector molecules are administered by expression from one or more expression constructs delivered to the vertebrate cell.

4. The method of claim 3, wherein the one or more expression constructs further comprise one or more RNA polymerase III promoters positioned within the constructs, and wherein the one or more RNA polymerase III promoters drive the expression of at least one said dsRNA effector molecule.

5. The method of claim 4, wherein at least one of the expression constructs comprises at least two different RNA polymerase III promoters.

6. The method of claim 4, wherein at least one of the expression constructs comprises at least three RNA polymerase III promoters, wherein said at least three RNA polymerase III promoters may be the same or different.

7. The method of claim 3, wherein at least one of the expression constructs encodes at least two dsRNA effector molecules.

8. The method of claim 3, wherein one expression construct encodes all of the dsRNA effector molecules administered.

9. A method of inhibiting the replication of HCV in a vertebrate cell infected by said virus, the method comprising administering to said vertebrate cell
- a first dsRNA effector molecule comprising an effector molecule consisting of SEQ ID NO: 7 and an effector complement of SEQ ID NO: 7,
- a second dsRNA effector molecule comprising an effector sequence consisting of SEQ ID NO: 59 and an effector complement of SEQ ID NO: 59,
- a third dsRNA effector molecule comprising an effector sequence consisting of SEQ ID NO: 17 and an effector complement of SEQ ID NO: 17, and
- a fourth dsRNA effector molecule comprising an effector sequence consisting of SEQ ID NO: 19 and an effector complement of SEQ ID NO: 19,
- wherein U is substituted for T.

10. The method of claim 9, wherein the vertebrate cell is a human cell.

11. The method of claim 9, wherein the dsRNA effector molecules are administered by expression from one or more expression constructs in the cell, and at least one of said one or more expression constructs comprising a plurality of RNA polymerase III promoters positioned within the construct to drive the expression of a plurality of said dsRNA effector molecules.

12. A method of inhibiting the replication of HCV in a vertebrate cell infected by said virus, the method comprising administering to said vertebrate cell
- a first dsRNA effector molecule comprising an effector molecule consisting of SEQ ID NO: 7 and an effector complement of SEQ ID NO: 7,
- a second dsRNA effector molecule comprising an effector sequence consisting of SEQ ID NO: 59 and an effector complement of SEQ ID NO: 59,
- a third dsRNA effector molecule comprising an effector sequence consisting of SEQ ID NO: 22 and an effector complement of SEQ ID NO: 22, and
- a fourth dsRNA effector molecule comprising an effector sequence consisting of SEQ ID NO: 23 and an effector complement of SEQ ID NO: 23,
- wherein U is substituted for T.

13. The method of claim 1, wherein the dsRNA effector molecules are short hairpin (sh)RNA.

14. The method of claim 11, wherein at least one of the expression constructs encodes at least two dsRNA effector molecules.

15. The method of claim 11, wherein one expression construct encodes all of the dsRNA effector molecules administered.

16. The method of claim 9, wherein the dsRNA effector molecules are short hairpin (sh)RNA effector molecules.

17. The method of claim 12, wherein the vertebrate cell is a human cell.

18. The method of claim 12, wherein the dsRNA effector molecules are administered by expression from one or more expression constructs in the cell, and at least one of said one or more expression constructs comprising a plurality of RNA polymerase III promoters positioned within the construct to drive the expression of a plurality of the dsRNA effector molecules.

19. The method of claim 18, wherein at least one of the expression constructs encodes at least two dsRNA effector molecules.

20. The method of claim 18, wherein one expression construct encodes all of the dsRNA effector molecules administered.

21. The method of claim 12, wherein the dsRNA effector molecules are short hairpin (sh)RNA effector molecules.

* * * * *

SEQUENCE LISTING

<160> NUMBER OF SEQ ID NOS: 62

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Nucleotides
      9382-9402 of the HCV 3' NTR -continued

<400> SEQUENCE: 1
gctaaacact ccaggccaat a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Nucleotides
      9502-9522 of the HCV 3' NTR

<400> SEQUENCE: 2
tcctttggtg gctccatctt a                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Nucleotides
      9512-9532 of the HCV 3' NTR

<400> SEQUENCE: 3
gctccatctt agccctagtc a                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Nucleotides
      9518-9538 of the HCV 3' NTR

<400> SEQUENCE: 4
tcttagccct agtcacggct a                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Nucleotides
      9525-9545 of the HCV 3' NTR

<400> SEQUENCE: 5
cctagtcacg gctagctgtg a                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Nucleotides
      9526-9546 of the HCV 3' NTR

<400> SEQUENCE: 6
ctagtcacgg ctagctgtga a                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Nucleotides
      9552-9572 of the HCV 3' NTR

```
<400> SEQUENCE: 7
cgtgagccgc ttgactgcag a                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Nucleotides
      9577-9597 of the HCV 3' NTR

<400> SEQUENCE: 8
gctgatactg gcctctctgc a                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Nucleotides
      9579-9599 of the HCV 3' NTR

<400> SEQUENCE: 9
tgatactggc ctctctgcag a                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Nucleotides
      9583-9603 of the HCV 3' NTR

<400> SEQUENCE: 10
actggcctct ctgcagatca a                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Nucleotides
      9509-9529 of the HCV 3' NTR

<400> SEQUENCE: 11
gtggctccat cttagcccta g                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Nucleotides
      9520-9540 of the HCV 3' NTR

<400> SEQUENCE: 12
ttagccctag tcacggctag c                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Nucleotides
      9534-9554 of the HCV 3' NTR

<400> SEQUENCE: 13
```
ggctagctgt gaaaggtccg t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Nucleotides
      9560-9580 of the HCV 3' NTR

<400> SEQUENCE: 14
gcttgactgc agagagtgct g                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Nucleotides
      9581-9601 of the HCV 3' NTR

<400> SEQUENCE: 15
atactggcct ctctgcagat c                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Nucleotides
      9506-9526 of the HCV 3' NTR

<400> SEQUENCE: 16
ttggtggctc catcttagcc c                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Nucleotides
      9514-9534 of the HCV 3' NTR

<400> SEQUENCE: 17
tccatcttag ccctagtcac g                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Nucleotides
      9520-9540 of the HCV 3' NTR

<400> SEQUENCE: 18
ttagccctag tcacggctag c                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Nucleotides
      9537-9557 of the HCV 3' NTR

<400> SEQUENCE: 19

-continued tagctgtgaa aggtccgtga g                                              21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Nucleotides
      9544-9563 of the HCV 3' NTR

<400> SEQUENCE: 20
gaaaggtccg tgagccgctt                                                20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Nucleotides
      9554-9574 of the HCV 3' NTR

<400> SEQUENCE: 21
tgagccgctt gactgcagag a                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Nucleotides
      9567-9587 of the HCV 3' NTR

<400> SEQUENCE: 22
tgcagagagt gctgatactg g                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Nucleotides
      9584-9604 of the HCV 3' NTR

<400> SEQUENCE: 23
ctggcctctc tgcagatcaa g                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 1

<400> SEQUENCE: 24
cctgtgagga actactgtct t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA minus strand region 1

<400> SEQUENCE: 25
atcactcccc tgtgaggaac t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 1

<400> SEQUENCE: 26
acgcagaaag cgtctagcca t                                          21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA minus strand region 1

<400> SEQUENCE: 27
ttcacgcaga aagcgtctag c                                          21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 1

<400> SEQUENCE: 28
cgtctagcca tggcgttagt a                                          21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA minus strand region 1

<400> SEQUENCE: 29
tagccatggc gttagtatga g                                          21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 1

<400> SEQUENCE: 30
gtctagccat ggcgttagta t                                          21

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: HCV 5' UTR
      siRNA minus strand region 1

<400> SEQUENCE: 31
atcactcccc tgtgaggaac tactg                                      25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: HCV 5' UTR
      siRNA plus strand region 1

<400> SEQUENCE: 32
ctcccctgtg aggaactact gtctt                                             25

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: HCV 5' UTR
      siRNA minus strand region 1

<400> SEQUENCE: 33
atcactcccc tgtgaggaac tactgtc                                           27

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: HCV 5' UTR
      siRNA plus strand region 1

<400> SEQUENCE: 34
gaggaactac tgtcttcacg cagaa                                             25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: HCV 5' UTR
      siRNA minus strand region 1

<400> SEQUENCE: 35
aactactgtc ttcacgcaga aagcg                                             25

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: HCV 5' UTR
      siRNA plus strand region 1

<400> SEQUENCE: 36
gtgaggaact actgtcttca cgcagaa                                           27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: HCV 5' UTR
      siRNA minus strand region 1

<400> SEQUENCE: 37
aactactgtc ttcacgcaga aagcgtc                                           27

```
<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 2

<400> SEQUENCE: 38
gagccatagt ggtctgcgga a                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA minus strand region 2

<400> SEQUENCE: 39
atagtggtct gcggaaccgg t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 2

<400> SEQUENCE: 40
gaaccggtga gtacaccgga a                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA minus strand region 2

<400> SEQUENCE: 41
tagtggtctg cggaaccggt g                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 2

<400> SEQUENCE: 42
accggtgagt acaccggaat t                                              21

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: HCV 5' UTR
      siRNA minus strand region 2

<400> SEQUENCE: 43
aaccggtgag tacaccggaa ttgcc                                          25

<210> SEQ ID NO 44
```

-continued

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: HCV 5' UTR
      siRNA plus strand region 2

<400> SEQUENCE: 44
gggagagcca tagtggtctg cggaa                                              25

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 5

<400> SEQUENCE: 45
ggccttgtgg tactgcctga t                                                  21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA minus strand region 5

<400> SEQUENCE: 46
aaaggccttg tggtactgcc t                                                  21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 5

<400> SEQUENCE: 47
gccttgtggt actgcctgat a                                                  21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA minus strand region 5

<400> SEQUENCE: 48
aaggccttgt ggtactgcct g                                                  21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA plus strand region 5

<400> SEQUENCE: 49
gtactgcctg atagggtgct t                                                  21

<210> SEQ ID NO 50
<211> LENGTH: 21

```
<212> TYPE: DNA
<213> ORGANISM: Artificial Sequence
<220> FEATURE:
<223> OTHER INFORMATION: Description of Artificial Sequence: HCV 5' UTR
      siRNA minus strand region 5

<400> SEQUENCE: 50
ttgtggtact gcctgatagg g                                           21

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: HCV 5' UTR
      siRNA plus strand region 5

<400> SEQUENCE: 51
aaggccttgt ggtactgcct gataggg                                     27

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: HCV 5' UTR
      siRNA minus strand region 5

<400> SEQUENCE: 52
tactgcctga tagggtgctt g                                           21

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: HCV 5' UTR
      siRNA plus strand region 5

<400> SEQUENCE: 53
cgaaaggcct tgtggtactg cctgata                                     27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: HCV 5' UTR
      siRNA minus strand region 5

<400> SEQUENCE: 54
ttgtggtact gcctgatagg gtgcttg                                     27

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: HCV 5' UTR
      siRNA plus strand region 5

<400> SEQUENCE: 55
cttgcgagtg ccccgggagg tctcgta                                     27

<210> SEQ ID NO 56
<211> LENGTH: 25
<212> TYPE: DNA
```

```
<213> ORGANISM: Artificial Sequence
<220> FEATURE:
<223> OTHER INFORMATION: Description of Artificial Sequence: HCV 5' UTR
      siRNA minus strand region 5

<400> SEQUENCE: 56
tactgcctga tagggtgctt gcgag                                            25

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: HCV 5' UTR
      siRNA minus strand region 5

<400> SEQUENCE: 57
tagggtgctt gcgagtgccc cggg                                             24

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: HCV 5' UTR
      siRNA minus strand region 5

<400> SEQUENCE: 58
ttgcgagtgc cccgggaggt ctcgtag                                          27

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: HCV 3' UTR
      conserved region sequence

<400> SEQUENCE: 59
ggtggctcca tcttagccct a                                                21

<210> SEQ ID NO 60
<211> LENGTH: 58
<212> TYPE: DNA
<213> ORGANISM: Artificial Sequence
<220> FEATURE:
<223> OTHER INFORMATION: Description of Artificial Sequence: Nucleotides
      9502-9559 of the HCV 3' NTR

<400> SEQUENCE: 60
tcctttggtg gctccatctt agccctagtc acggctagct gtgaaaggtc cgtgagcc        58

<210> SEQ ID NO 61
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggctcacgga cctttcacag ctagccgtga ctagggctaa gatggagcca ccaaagga        58

<210> SEQ ID NO 62
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 62
gctagccgtg actagggcta a                                              21
```